(12) United States Patent
Boettcher et al.

(10) Patent No.: US 11,967,222 B2
(45) Date of Patent: *Apr. 23, 2024

(54) CONFIGURING A SMART HOME CONTROLLER

(71) Applicant: Google LLC, Mountain View, CA (US)

(72) Inventors: Jesse William Boettcher, San Jose, CA (US); Sophie Solveig Le Guen, Burlingame, CA (US); Jason Rundle Rukes, San Francisco, CA (US); Ted Stephen Boda, San Jose, CA (US); David Sloo, Menlo Park, CA (US)

(73) Assignee: Google LLC, Mountain View, CA (US)

( * ) Notice: Subject to any disclaimer, the term of this patent is extended or adjusted under 35 U.S.C. 154(b) by 15 days.

This patent is subject to a terminal disclaimer.

(21) Appl. No.: 17/649,922

(22) Filed: Feb. 3, 2022

(65) Prior Publication Data
US 2022/0157155 A1   May 19, 2022

Related U.S. Application Data

(63) Continuation of application No. 16/787,575, filed on Feb. 11, 2020, now abandoned, which is a
(Continued)

(51) Int. Cl.
*G08B 29/18* (2006.01)
*A01N 1/02* (2006.01)
(Continued)

(52) U.S. Cl.
CPC ........... *G08B 29/185* (2013.01); *A01N 1/021* (2013.01); *A01N 1/0284* (2013.01);
(Continued)

(58) Field of Classification Search
CPC .. G08B 29/185; G08B 13/196; G08B 25/001; G08B 25/08; A01N 1/021; A01N 1/0284; C07K 14/705; C12N 5/00; C12N 5/067; C12N 5/069; C12N 15/85; C12N 2510/00; G01N 33/5008; G01N 2333/705; G05B 15/02; G05B 2219/2642
See application file for complete search history.

(56) References Cited

U.S. PATENT DOCUMENTS 5,790,015 A * 8/1998 Iitsuka ............... G07C 9/00182
340/425.5
5,801,625 A    9/1998 Wang
(Continued)

FOREIGN PATENT DOCUMENTS

EP    2393071 A2    12/2011

*Primary Examiner* — Steven Lim
*Assistant Examiner* — Son M Tang
(74) *Attorney, Agent, or Firm* — Kilpatrick Townsend & Stockton LLP

(57) ABSTRACT

A method performed at a computer system includes: obtaining door lock activation data for a door of a dwelling of the user; obtaining current occupancy data for the dwelling; setting a configuration of a controller for the dwelling, based at least in part on the door lock activation data for the door and the current occupancy data for the dwelling; the first configuration including for each sensor in a set of sensors coupled to the controller, disabling the sensor or disabling alerts from the sensor.

17 Claims, 12 Drawing Sheets

Related U.S. Application Data continuation of application No. 16/174,077, filed on Oct. 29, 2018, now Pat. No. 10,559,192, which is a continuation of application No. 15/882,826, filed on Jan. 29, 2018, now Pat. No. 10,115,297, which is a continuation of application No. 14/672,012, filed on Mar. 27, 2015, now Pat. No. 9,911,318.

(51) Int. Cl.

| | | |
|---|---|---|
| *C07K 14/705* | (2006.01) | |
| *C12N 5/00* | (2006.01) | |
| *C12N 5/071* | (2010.01) | |
| *C12N 15/85* | (2006.01) | |
| *G01N 33/50* | (2006.01) | |
| *G05B 15/02* | (2006.01) | |
| *G08B 13/00* | (2006.01) | |
| *G08B 13/196* | (2006.01) | |
| *G08B 25/00* | (2006.01) | |
| *G08B 25/08* | (2006.01) | |

(52) U.S. Cl.
CPC .............. *C07K 14/705* (2013.01); *C12N 5/00* (2013.01); *C12N 5/067* (2013.01); *C12N 5/069* (2013.01); *C12N 15/85* (2013.01); *G01N 33/5008* (2013.01); *G05B 15/02* (2013.01); *G08B 13/00* (2013.01); *G08B 13/196* (2013.01); *G08B 25/001* (2013.01); *G08B 25/08* (2013.01); *C12N 2510/00* (2013.01); *G01N 2333/705* (2013.01); *G05B 2219/2642* (2013.01)

(56) References Cited

U.S. PATENT DOCUMENTS

| | | | |
|---|---|---|---|
| 6,076,385 A | 6/2000 | Pedroso et al. | |
| 6,225,903 B1 * | 5/2001 | Soloway | G08B 25/008 340/5.1 |
| 6,331,816 B1 | 12/2001 | Myllymaki | |
| 6,658,572 B1 | 12/2003 | Craig | |
| 6,909,921 B1 | 6/2005 | Bilger | |
| 8,063,764 B1 | 11/2011 | Mihailidis et al. | |
| 8,373,555 B1 | 2/2013 | Redden et al. | |
| 8,810,392 B1 | 8/2014 | Teller et al. | |
| 9,064,394 B1 | 6/2015 | Trundle | |
| 9,235,976 B2 * | 1/2016 | Sloo | F24F 11/33 |
| 2003/0071724 A1 | 4/2003 | D'Amico | |
| 2003/0098789 A1 | 5/2003 | Murakami et al. | |
| 2005/0225442 A1 * | 10/2005 | Kanayama | G08B 25/008 340/539.13 |
| 2006/0025132 A1 | 2/2006 | Karaoguz et al. | |
| 2007/0076095 A1 * | 4/2007 | Tomaszewski | G08B 25/008 348/E7.087 |
| 2007/0182543 A1 | 8/2007 | Luo | |
| 2007/0247302 A1 * | 10/2007 | Martin | G08B 25/008 340/506 |
| 2008/0238669 A1 | 10/2008 | Linford | |
| 2009/0146846 A1 | 6/2009 | Grossman | |
| 2010/0081375 A1 | 4/2010 | Rosenblatt et al. | |
| 2010/0156608 A1 | 6/2010 | Bae et al. | |
| 2010/0161720 A1 | 6/2010 | Colligan et al. | |
| 2010/0283579 A1 | 11/2010 | Kraus et al. | |
| 2010/0289644 A1 | 11/2010 | Slavin et al. | |
| 2012/0127980 A1 | 5/2012 | Quinn | |
| 2013/0057404 A1 | 3/2013 | Thibault | |
| 2013/0073094 A1 | 3/2013 | Knapton et al. | |
| 2013/0293718 A1 * | 11/2013 | M | G08B 13/19669 340/541 |
| 2014/0167929 A1 | 6/2014 | Shim et al. | |
| 2014/0266669 A1 | 9/2014 | Fadell et al. | |
| 2014/0280865 A1 | 9/2014 | Albertson et al. | |
| 2015/0015395 A1 | 1/2015 | Liang et al. | |
| 2015/0109104 A1 * | 4/2015 | Fadell | G08B 27/005 340/5.7 |
| 2015/0116107 A1 * | 4/2015 | Fadell | G06Q 10/083 340/501 |
| 2015/0116111 A1 | 4/2015 | Foster | |
| 2015/0161882 A1 | 6/2015 | Lett | |
| 2015/0279198 A1 * | 10/2015 | Gu | G08B 25/008 340/541 |
| 2015/0308706 A1 | 10/2015 | Bunker et al. | |
| 2015/0309487 A1 * | 10/2015 | Lyman | G05B 15/02 700/275 |
| 2016/0189528 A1 | 6/2016 | Lee et al. | |
| 2022/0108578 A1 * | 4/2022 | Yakota | G07C 9/38 |

* cited by examiner

900

912 In accordance with a determination that the door was locked from outside the dwelling, and the user is not present in the dwelling, set or send instructions to set the configuration of the controller for the dwelling to a second configuration, distinct from the first configuration, the second configuration having the one or more door sensors and/or window sensors for the dwelling enabled and having the one or more motion sensors for the dwelling enabled.

920 The second configuration has one or more video cameras in the dwelling enabled, and notifications from the one or more video cameras in the dwelling enabled.

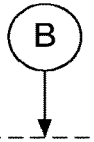

922 In accordance with a determination that the door was locked from inside the dwelling, the user is not present in the dwelling, and the dwelling is unoccupied, set or send instructions to set the configuration of the controller for the dwelling to the second configuration.

924 In accordance with a determination that the door is unlocked, the user is not present within a geo-fence around the dwelling, and the dwelling is unoccupied, set or send instructions to set the configuration of the controller for the dwelling to the second configuration, and lock or send instructions to lock one or more doors in the dwelling.

926 In accordance with a determination that the door is unlocked, the user is not present within a geo-fence around the dwelling, and the dwelling is unoccupied, set or send instructions to set the configuration of the controller for the dwelling to the second configuration, lock or send instructions to lock one or more doors in the dwelling, and send a notification to the user that the controller has been placed in the second configuration.

928 A housing that contains the computer system also contains a door lock for the door.

930 The computer system is the smart home controller.

932 The computer system is located in a smart home provider server system remote from the dwelling.

CONFIGURING A SMART HOME CONTROLLER

RELATED APPLICATIONS

This application is a continuation of U.S. patent application Ser. No. 16/787,575, filed Feb. 11, 2020, entitled "Configuring a Smart Home Controller," which is a continuation of U.S. patent application Ser. No. 16/174,077, filed Oct. 29, 2018, entitled "Configuring a Smart Home Controller," which is a continuation of U.S. patent application Ser. No. 15/882,826, filed Jan. 29, 2018, entitled "Configuring a Smart Home Controller" and issued as U.S. Pat. No. 10,115,297 on Oct. 30, 2018, which is a continuation of U.S. patent application Ser. No. 14/672,012, filed Mar. 27, 2015, entitled "Configuring a Smart Home Controller" and issued as U.S. Pat. No. 9,911,318 on Mar. 6, 2018, each of which is hereby incorporated by reference in its entirety.

TECHNICAL FIELD

This relates generally to detection of the presence of a person in a structure, including but not limited to setting the configuration of a smart structure controller based on the detection.

BACKGROUND

A home or other dwelling may be equipped with a system of sensors and a controller. The controller is often set manually to one of a number of a predefined configurations, in order to detect various parameters and states, such as user location, occupancy, the status of a door or window, and so forth. The data gathered by the system in a given configuration may be used, for example, to shut off unneeded electricity use to save electricity and/or to warn of potentially dangerous conditions and intruders. However, the configuration being used may need to change as circumstances in the dwelling change. For example, a configuration that has certain sensors always on can lead to false alarms, as well as inconvenience for the occupants of the dwelling. Reducing false alarms and increasing convenience is important for the effectiveness and user satisfaction with such systems. Yet current manual methods for setting the configuration of the controller are inefficient and inconvenient for users.

SUMMARY

Accordingly, there is a need for improved devices and methods for setting the configuration of a smart home controller. Such devices and methods optionally complement or replace conventional devices and methods for setting the configuration of a smart home controller.

In accordance with some embodiments, a method is performed at a computing system with one or more processors and memory. The method includes: obtaining current location data for a user; determining whether the user is within a predefined distance from a dwelling of the user based at least in part on the received current location data; obtaining door lock activation data for a door of the dwelling; determining whether the door is currently locked or unlocked based at least in part on the received door lock activation data; obtaining current occupancy data for the dwelling of the user; determining whether the dwelling is currently occupied based at least in part on the received occupancy data; setting a configuration of a controller for the dwelling to a first configuration based at least in part on two or more of: (i) the determination of whether the user is within a predefined distance from the dwelling, (ii) the determination of whether the door is currently locked or unlocked, or (iii) the determined occupancy for the dwelling, the first configuration including for each sensor in a set of sensors coupled to the controller, disabling the sensor or disabling alerts from the sensor; while the controller is operating in the first configuration: in accordance with a determination that the user is not within the predefined distance from the dwelling and that the door is currently unlocked, setting or sending instructions to set the configuration of the controller to a second configuration, the second configuration including for each sensor in the set of sensors coupled to the controller, enabling the sensor or enabling alerts from the sensor; in accordance with setting, or sending instructions to set, the configuration of the controller to the second configuration, sending a notification to the user that the controller has been set to the second configuration.

In accordance with some embodiments, a computing system includes one or more processors, memory, and one or more programs; the one or more programs are stored in the memory and configured to be executed by the one or more processors and the one or more programs include instructions for performing the operations of the method described above. In accordance with some embodiments, a non-transitory computer readable storage medium has stored therein instructions which when executed by a computing system with one or more processors, cause the computing system to perform the operations of the method described above. In accordance with some embodiments, a computing system includes means for performing the operations of the method described above.

Thus, computing systems are provided with more efficient methods for setting the configuration of a smart home controller, thereby increasing the effectiveness, efficiency, and user satisfaction with such systems. Such methods and devices may complement or replace conventional methods for setting the configuration of a smart home controller.

BRIEF DESCRIPTION OF THE DRAWINGS

For a better understanding of the various described embodiments, reference should be made to the Description of Embodiments below, in conjunction with the following drawings in which like reference numerals refer to corresponding parts throughout the figures.

FIGS. 8A-8B and 9A-9C are flow diagrams illustrating methods of setting a configuration of a smart home controller in accordance with some embodiments.

DESCRIPTION OF EMBODIMENTS

Figure 1:
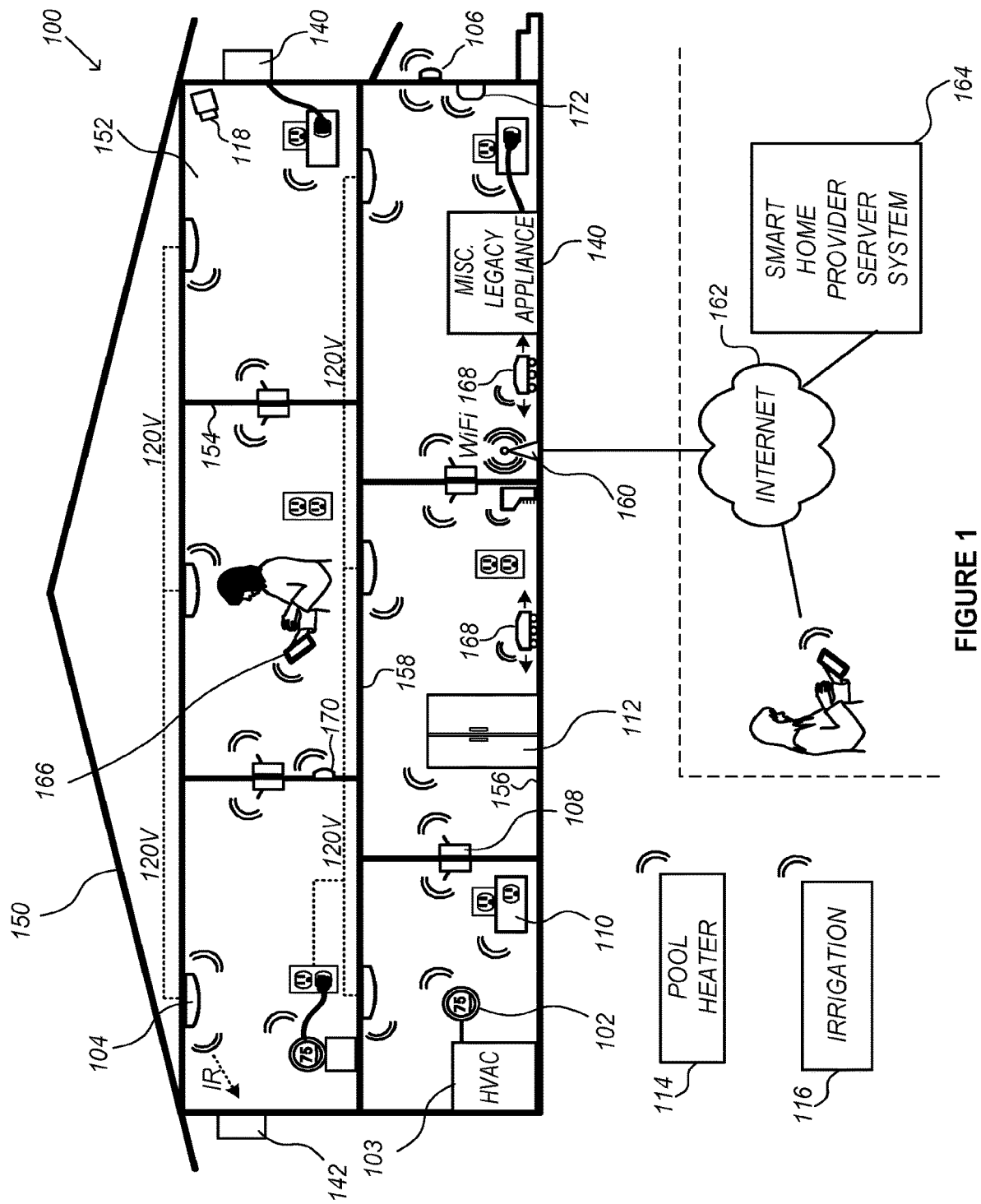
FIG. 1 is an example of a smart home environment in accordance with some embodiments.

As noted above, there is a need for improved devices and methods for setting the configuration of a smart home controller. Here, a computing system sets, or sends instructions to set, a configuration of a controller for a dwelling in accordance with a determination with respect to particular parameters. This determination is based at least in part on occupancy data for the dwelling, the current location of the user, and lock activation data for one or more locks of the dwelling. Within a respective configuration, respective sensors in the dwelling are enabled or disabled. Additional operations may be performed in addition to setting the configuration.

The various embodiments described herein include systems, methods and/or computer readable storage medium used to configure a smart home controller.

(A1) In some embodiments, a method includes, at a computer system with one or more processors and memory: receiving current location data for a user; receiving door lock activation data for a door of a dwelling of the user; receiving current occupancy data for the dwelling of the user; determining a configuration of a controller for the dwelling, based at least in part on the received current location data for the user, the received door lock activation data for the door, and the received current occupancy data for the dwelling of the user; in accordance with a determination that the door was locked from inside the dwelling, and the user is present in the dwelling, setting or sending instructions to set a configuration of the controller for the dwelling to a first configuration, the first configuration having one or more door sensors and/or window sensors for the dwelling enabled and having one or more motion sensors for the dwelling disabled; and, in accordance with a determination that the door was locked from outside the dwelling, and the user is not present in the dwelling, setting or sending instructions to set the configuration of the controller for the dwelling to a second configuration, distinct from the first configuration, the second configuration having the one or more door sensors and/or window sensors for the dwelling enabled and having the one or more motion sensors for the dwelling enabled.

(A2) In some embodiments of the method of A1, receiving current location data for the user includes receiving current location data for the user from one or more sensors in the dwelling of the user.

(A3) In some embodiments of the method of any of A1 to A2, receiving current location data for the user includes receiving current location data for the user from a smart phone of the user.

(A4) In some embodiments of the method of any of A1 to A3, the first configuration has one or more video cameras in the dwelling enabled, but notifications from the one or more video cameras in the dwelling disabled.

(A5) In some embodiments of the method of any of A1 to A4, the second configuration has one or more video cameras in the dwelling enabled, and notifications from the one or more video cameras in the dwelling enabled.

(A6) In some embodiments of the method of any of A1 to A5, the method includes: in accordance with a determination that the door was locked from inside the dwelling, the user is not present in the dwelling, and the dwelling is unoccupied, setting or sending instructions to set the configuration of the controller for the dwelling to the second configuration.

(A7) In some embodiments of the method of any of A1 to A6, the method includes: in accordance with a determination that the door is unlocked, the user is not present within a geo-fence around the dwelling, and the dwelling is unoccupied, setting or sending instructions to set the configuration of the controller for the dwelling to the second configuration, and locking or sending instructions to lock one or more doors in the dwelling.

(A8) In some embodiments of the method of any of A1 to A7, the method includes: in accordance with a determination that the door is unlocked, the user is not present within a geo-fence around the dwelling, and the dwelling is unoccupied, setting or sending instructions to set the configuration of the controller for the dwelling to the second configuration, locking or sending instructions to lock one or more doors in the dwelling, and sending a notification to the user that the controller has been placed in the second configuration.

(A9) In some embodiments of the method of any of A1 to A8, a housing that contains the computer system also contains a door lock for the door.

(A10) In some embodiments of the method of any of A1 to A9, the computer system is the smart home controller.

(A11) In some embodiments of the method of any of A1 to A8, the computer system is located in a smart home provider server system remote from the dwelling.

(A12) In another aspect, a computer system includes one or more processors; memory; and one or more programs, wherein the one or more programs are stored in the memory and configured to be executed by the one or more processors, the one or more programs including instructions for performing any of the methods A1 to A12 described herein.

(A13) In another aspect, a computer readable storage medium stores one or more programs, the one or more programs comprising instructions, which when executed by a computer system, cause the computer system to perform any of the methods A1 to A12 described herein.

Figure 5:
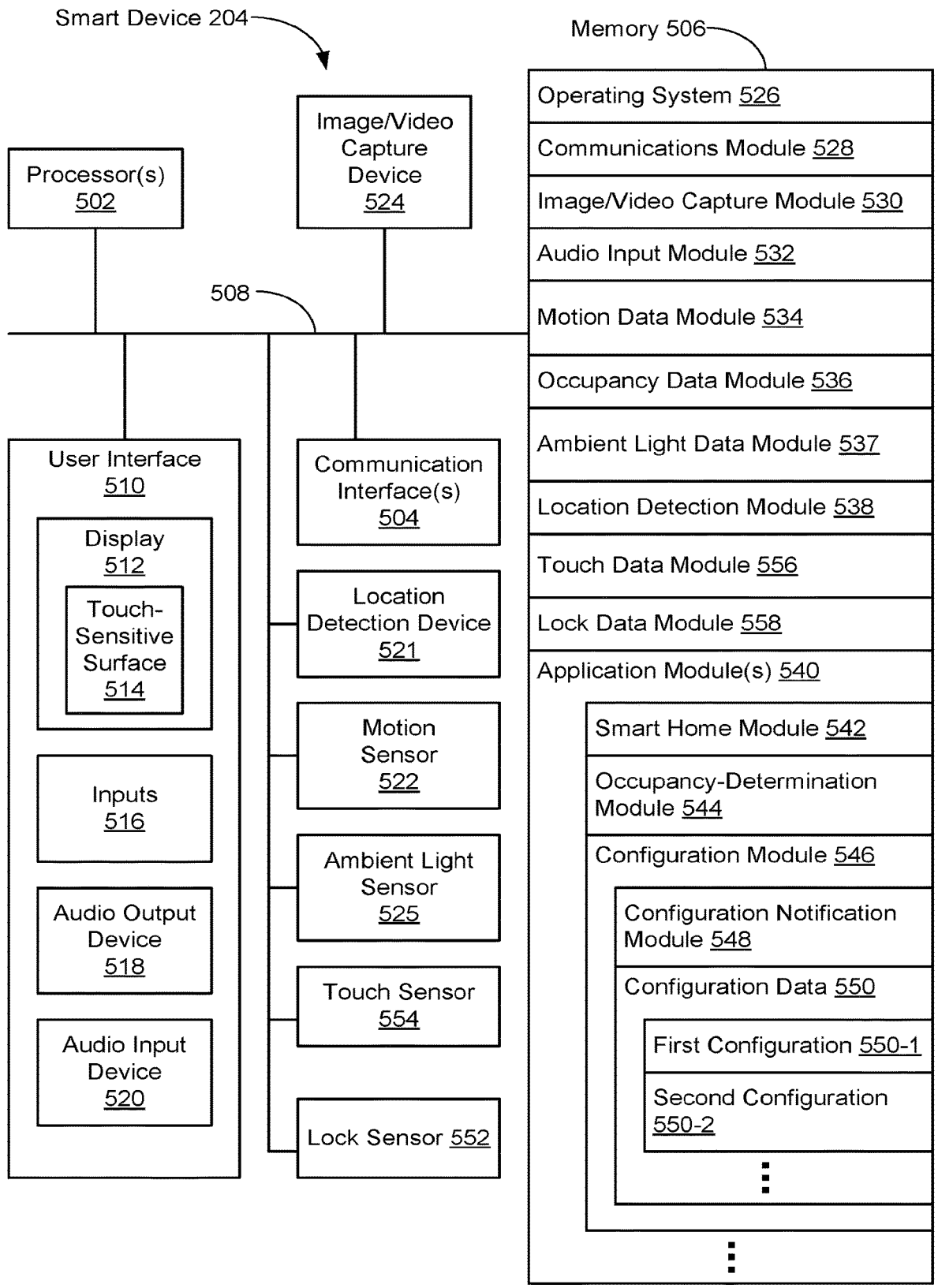
FIG. 5 is a block diagram illustrating an example of a smart device in accordance with some embodiments.
Figure 6:
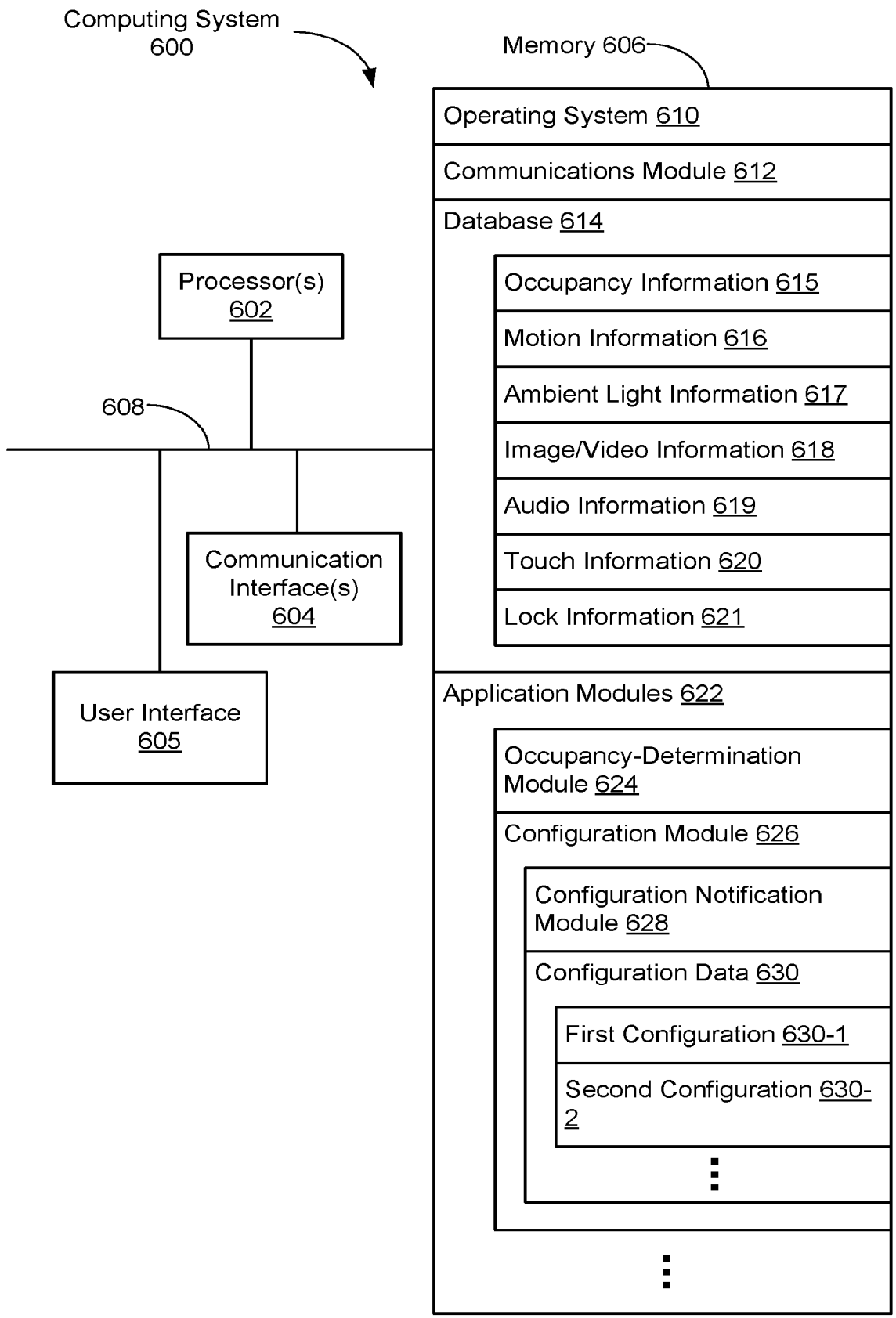
FIG. 6 is a block diagram illustrating an example of a computing system in accordance with some embodiments.
Figure 7:
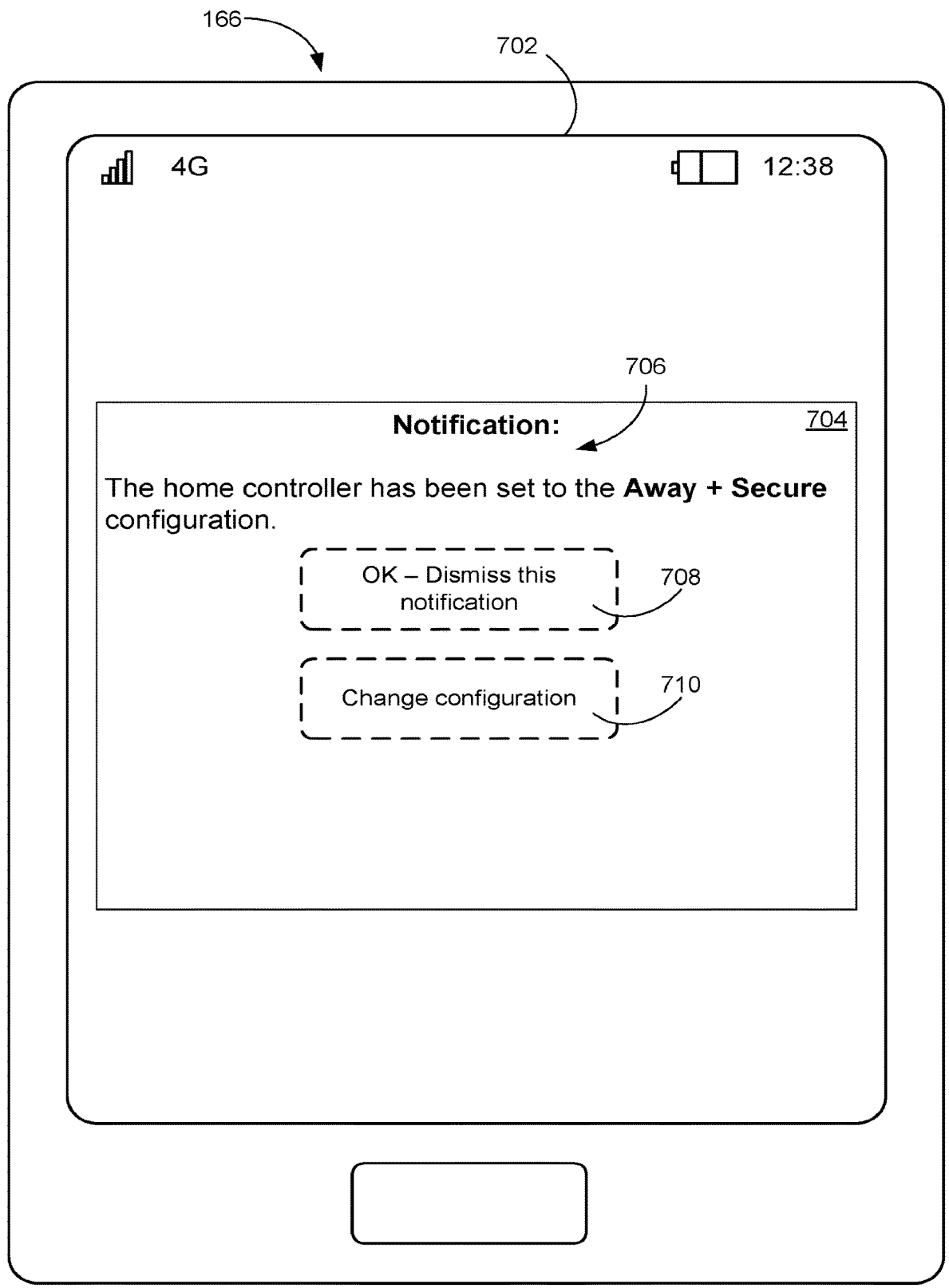
FIG. 7 illustrates an example of a graphical user interface shown on an electronic device in accordance with some embodiments.

Below, FIGS. 1-4 provide an overview of example smart home device networks and capabilities. FIGS. 5-6 are block diagrams of electronic devices included in or in communication with a smart home environment. FIG. 7 illustrates an example of a user interface for displaying a notification associated with a configuration. FIGS. 8A-8B and 9A-9C are flow diagrams illustrating methods of setting a configuration of a smart home controller in accordance with some embodiments.

Reference will now be made in detail to embodiments, examples of which are illustrated in the accompanying drawings. In the following detailed description, numerous specific details are set forth in order to provide a thorough understanding of the various described embodiments. However, it will be apparent to one of ordinary skill in the art that the various described embodiments may be practiced without these specific details. In other instances, well-known methods, procedures, components, circuits, and networks have not been described in detail so as not to unnecessarily obscure aspects of the embodiments.

It will also be understood that, although the terms first, second, etc. are, in some instances, used herein to describe various elements, these elements should not be limited by these terms. These terms are only used to distinguish one element from another. For example, a first configuration could be termed a second configuration, and, similarly, a second configuration could be termed a first configuration, without departing from the scope of the various described embodiments. The first configuration and the second configuration are both configurations, but they are not the same configuration.

The terminology used in the description of the various described embodiments herein is for the purpose of describing particular embodiments only and is not intended to be limiting. As used in the description of the various described embodiments and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "includes," "including," "comprises," and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" is, optionally, construed to mean "when" or "upon" or "in response to determining" or "in response to detecting" or "in accordance with a determination that," depending on the context. Similarly, the phrase "if it is determined" or "if [a stated condition or event] is detected" is, optionally, construed to mean "upon determining" or "in response to determining" or "upon detecting [the stated condition or event]" or "in response to detecting [the stated condition or event]" or "in accordance with a determination that [a stated condition or event] is detected," depending on the context.

It is to be appreciated that "smart home environments" may refer to smart environments for homes such as a single-family house, but the scope of the present teachings is not so limited. The present teachings are also applicable, without limitation, to duplexes, townhomes, multi-unit apartment buildings, hotels, retail stores, office buildings, industrial buildings, and more generally any living space or work space.

It is also to be appreciated that while the terms user, customer, installer, homeowner, occupant, guest, tenant, landlord, repair person, and the like may be used to refer to the person or persons acting in the context of some particularly situations described herein, these references do not limit the scope of the present teachings with respect to the person or persons who are performing such actions. Thus, for example, the terms user, customer, purchaser, installer, subscriber, and homeowner may often refer to the same person in the case of a single-family residential dwelling, because the head of the household is often the person who makes the purchasing decision, buys the unit, and installs and configures the unit, and is also one of the users of the unit. However, in other scenarios, such as a landlord-tenant environment, the customer may be the landlord with respect to purchasing the unit, the installer may be a local apartment supervisor, a first user may be the tenant, and a second user may again be the landlord with respect to remote control functionality. Importantly, while the identity of the person performing the action may be germane to a particular advantage provided by one or more of the embodiments, such identity should not be construed in the descriptions that follow as necessarily limiting the scope of the present teachings to those particular individuals having those particular identities.

FIG. 1 is an example of a smart home environment 100 in accordance with some embodiments. Smart home environment 100 includes a structure 150 (e.g., a house, office building, garage, or mobile home) with various integrated devices. It will be appreciated that devices may also be integrated into a smart home environment 100 that does not include an entire structure 150, such as an apartment, condominium, or office space. Further, the smart home environment 100 may control and/or be coupled to devices outside of the actual structure 150. Indeed, several devices in the smart home environment 100 need not be physically within the structure 150. For example, a device controlling a pool heater 114 or irrigation system 116 may be located outside of structure 150.

The depicted structure 150 includes a plurality of rooms 152, separated at least partly from each other via walls 154. The walls 154 may include interior walls or exterior walls. Each room may further include a floor 156 and a ceiling 158. Devices may be mounted on, integrated with and/or supported by a wall 154, floor 156 or ceiling 158.

In some embodiments, the integrated devices of the smart home environment 100 include intelligent, multi-sensing, network-connected devices, that integrate seamlessly with each other in a smart home network (e.g., 202 FIG. 2) and/or with a central server or a cloud-computing system to provide a variety of useful smart home functions. The smart home environment 100 may include one or more intelligent, multi-sensing, network-connected thermostats 102 (hereinafter referred to as "smart thermostats 102"), one or more intelligent, network-connected, multi-sensing hazard detection units 104 (hereinafter referred to as "smart hazard detectors 104"), and one or more intelligent, multi-sensing, network-connected entryway interface devices 106 (hereinafter referred to as "smart doorbells 106"). In some embodiments, the one or more smart thermostats 102 detect ambient climate characteristics (e.g., temperature and/or humidity) and control a HVAC system 103 accordingly. The one or more smart hazard detectors 104 may detect the presence of a hazardous substance or a substance indicative of a hazardous substance (e.g., smoke, fire, and/or carbon monoxide). The smart doorbell 106 may detect a person's approach to or departure from a location (e.g., an outer door), control doorbell functionality, announce a person's approach or departure via audio or visual means, and/or control settings on a security system (e.g., to activate or deactivate the security system when occupants go and come).

In some embodiments, the smart home environment 100 includes one or more intelligent, multi-sensing, network-connected door locks 172 (hereinafter referred to as "smart door locks 172"). Smart door lock 172 may be mounted on any type of door in the structure 150, including but not limited to swinging doors (e.g., a door between two adjacent rooms 152), sliding doors (e.g., a sliding glass door between a room and a balcony), and folding doors (e.g., a folding door between a room and a patio). A smart door lock 172 may be in either an unlocked or locked state. The state of smart door lock 172 may be changed from locked to unlocked, or vice versa, by a user and/or by a system or device (e.g., a smart home controller, a smart home provider server system) associated with the smart home environment 100. In some embodiments, the smart door lock 172 also includes one or more sensors capable of detecting occupancy of a room or enclosure.

In some embodiments, the smart home environment 100 includes one or more intelligent, multi-sensing, network-connected wall switches 108 (hereinafter referred to as "smart wall switches 108"), along with one or more intelligent, multi-sensing, network-connected wall plug interfaces 110 (hereinafter referred to as "smart wall plugs 110").

The smart wall switches 108 may detect ambient lighting conditions, detect room-occupancy states, and control a power and/or dim state of one or more lights. In some instances, smart wall switches 108 may also control a power state or speed of a fan, such as a ceiling fan. The smart wall plugs 110 may detect occupancy of a room or enclosure and control supply of power to one or more wall plugs (e.g., such that power is not supplied to the plug if nobody is at home).

In some embodiments, the smart home environment 100 of FIG. 1 includes a plurality of intelligent, multi-sensing, network-connected appliances 112 (hereinafter referred to as "smart appliances 112"), such as refrigerators, stoves, ovens, televisions, washers, dryers, lights, stereos, intercom systems, garage-door openers, floor fans, ceiling fans, wall air conditioners, pool heaters, irrigation systems, security systems, space heaters, window AC units, motorized duct vents, and so forth. In some embodiments, when plugged in, an appliance may announce itself to the smart home network, such as by indicating what type of appliance it is, and it may automatically integrate with the controls of the smart home. Such communication by the appliance to the smart home may be facilitated by either a wired or wireless communication protocol. The smart home may also include a variety of non-communicating legacy appliances 140, such as old conventional washer/dryers, refrigerators, and the like, which may be controlled by smart wall plugs 110. The smart home environment 100 may further include a variety of partially communicating legacy appliances 142, such as infrared ("IR") controlled wall air conditioners or other IR-controlled devices, which may be controlled by IR signals provided by the smart hazard detectors 104 or the smart wall switches 108.

In some embodiments, the smart home environment 100 includes one or more network-connected cameras 118 that are configured to provide video monitoring and security in the smart home environment 100. The cameras 118 may be used to determine occupancy of the structure 150 and/or particular rooms 152 in the structure 150, and thus may act as occupancy sensors or occupancy detection devices. For example, video captured by the cameras 118 may be processed to identify the presence of an occupant in the structure 150 (e.g., in a room 152). Specific individuals and/or categories of individuals (e.g., adult, child, etc.) may be identified based, for example, on their appearance (e.g., height, face) and/or movement (e.g., their walk/gate). The smart home environment 100 may additionally or alternatively include one or more other occupancy sensors or occupancy detection devices (e.g., the smart doorbell 106, smart door locks 172, touch screens, IR sensors, microphones, ambient light sensors, motion detectors or sensors, smart nightlights 170, optical sensors, audio sensors, touch sensors, etc.). In some embodiments, the smart home environment 100 includes radio-frequency identification (RFID) readers (e.g., in each room 152 or a portion thereof) that determine occupancy based on RFID tags located on or embedded in occupants. For example, RFID readers may be integrated into the smart hazard detectors 104. In some embodiments, the various sensors and devices that detect or determine occupancy generate occupancy data and transmit the occupancy data to other devices (e.g., a smart home controller, other smart device) in the smart home environment 100 or to the smart home provider server system 164. The occupancy data includes one or more of: motion data, video audio data, touch data, and RFID presence data.

The smart home environment 100 may also include communication with devices outside of the physical home but within a proximate geographical range of the home. For example, the smart home environment 100 may include a pool heater monitor 114 that communicates a current pool temperature to other devices within the smart home environment 100 and/or receives commands for controlling the pool temperature. Similarly, the smart home environment 100 may include an irrigation monitor 116 that communicates information regarding irrigation systems within the smart home environment 100 and/or receives control information for controlling such irrigation systems.

By virtue of network connectivity, one or more of the smart home devices of FIG. 1 may further allow a user to interact with the device even if the user is not proximate to the device. For example, a user may communicate with a device using a computer (e.g., a desktop computer, laptop computer, or tablet) or other portable electronic device (e.g., a mobile phone, such as a smart phone) 166. A webpage or application may be configured to receive communications from the user and control the device based on the communications and/or to present information about the device's operation to the user. For example, the user may view a current set point temperature for a device and adjust it using a computer. The user may be in the structure during this remote communication or outside the structure.

As discussed above, users may control smart devices in the smart home environment 100 using a network-connected computer or portable electronic device 166. In some examples, some or all of the occupants (e.g., individuals who live in the home) may register their device 166 with the smart home environment 100. Such registration may be made at a central server to authenticate the occupant and/or the device as being associated with the home and to give permission to the occupant to use the device to control the smart devices in the home. An occupant may use their registered device 166 to remotely control the smart devices of the home, such as when the occupant is at work or on vacation. The occupant may also use their registered device to control the smart devices when the occupant is actually located inside the home, such as when the occupant is sitting on a couch inside the home. It should be appreciated that instead of or in addition to registering devices 166, the smart home environment 100 may make inferences about which individuals live in the home and are therefore occupants and which devices 166 are associated with those individuals. As such, the smart home environment 100 may "learn" who is an occupant and permit the devices 166 associated with those individuals to control the smart devices of the home.

In some embodiments, one or more specific occupants are registered with the smart home environment 100 and categorized. For example, an occupant may be registered and assigned to one or more occupant categories (e.g., adult, child, disabled, elderly, etc.). The registration of an occupant may include detection by a camera 118 and corresponding data input using a device 166 to identify and categorize the occupant. The cameras 118 and other occupancy sensors and occupancy detection devices may be used to detect the specific occupants.

In some embodiments, in addition to containing processing and sensing capabilities, devices 102, 104, 106, 108, 110, 112, 114, 116, 118, 170, and/or 172 (collectively referred to as "the smart devices") are capable of data communications and information sharing with other smart devices, a central server or cloud-computing system, and/or other devices that are network-connected. Data communications may be carried out using any of a variety of custom or standard wireless protocols (e.g., IEEE 802.15.4, Wi-Fi, ZigBee, 6LoWPAN, Thread, Z-Wave, Bluetooth Smart, ISA100.11a, WirelessHART, MiWi, etc.) and/or any of a variety of custom or standard wired protocols (e.g., Ethernet, HomePlug, etc.), or any other suitable communication protocol, including communication protocols not yet developed as of the filing date of this document.

In some embodiments, the smart devices serve as wireless or wired repeaters. In some embodiments, a first one of the smart devices communicates with a second one of the smart devices via a wireless router. The smart devices may further communicate with each other via a connection (e.g., network interface 160) to a network, such as the Internet 162. Through the Internet 162, the smart devices may communicate with a smart home provider server system 164 (also called a central server system and/or a cloud-computing system herein). The smart home provider server system 164 may be associated with a manufacturer, support entity, or service provider associated with the smart device(s). In some embodiments, a user is able to contact customer support using a smart device itself rather than needing to use other communication means, such as a telephone or Internet-connected computer. In some embodiments, software updates are automatically sent from the smart home provider server system 164 to smart devices (e.g., when available, when purchased, or at routine intervals).

In some embodiments, the smart home environment 100 is set to one of multiple configurations. A configuration of the smart home environment 100 includes one or more settings and/or operations, including, for example, enabling and/or disabling particular sensors or smart devices, locking or unlocking a smart door lock 172, and so on. In some embodiments, the smart home environment 100 is set to a configuration by setting a controller for the structure 150 to the configuration. The controller set to the configuration performs the operations and activates the settings corresponding to the set configuration. The configuration may be set automatically by a device in the smart home environment 100 or manually by a user. In some embodiments, one or more users are sent a notification when the smart home environment 100 is set to a configuration.

Figure 2:
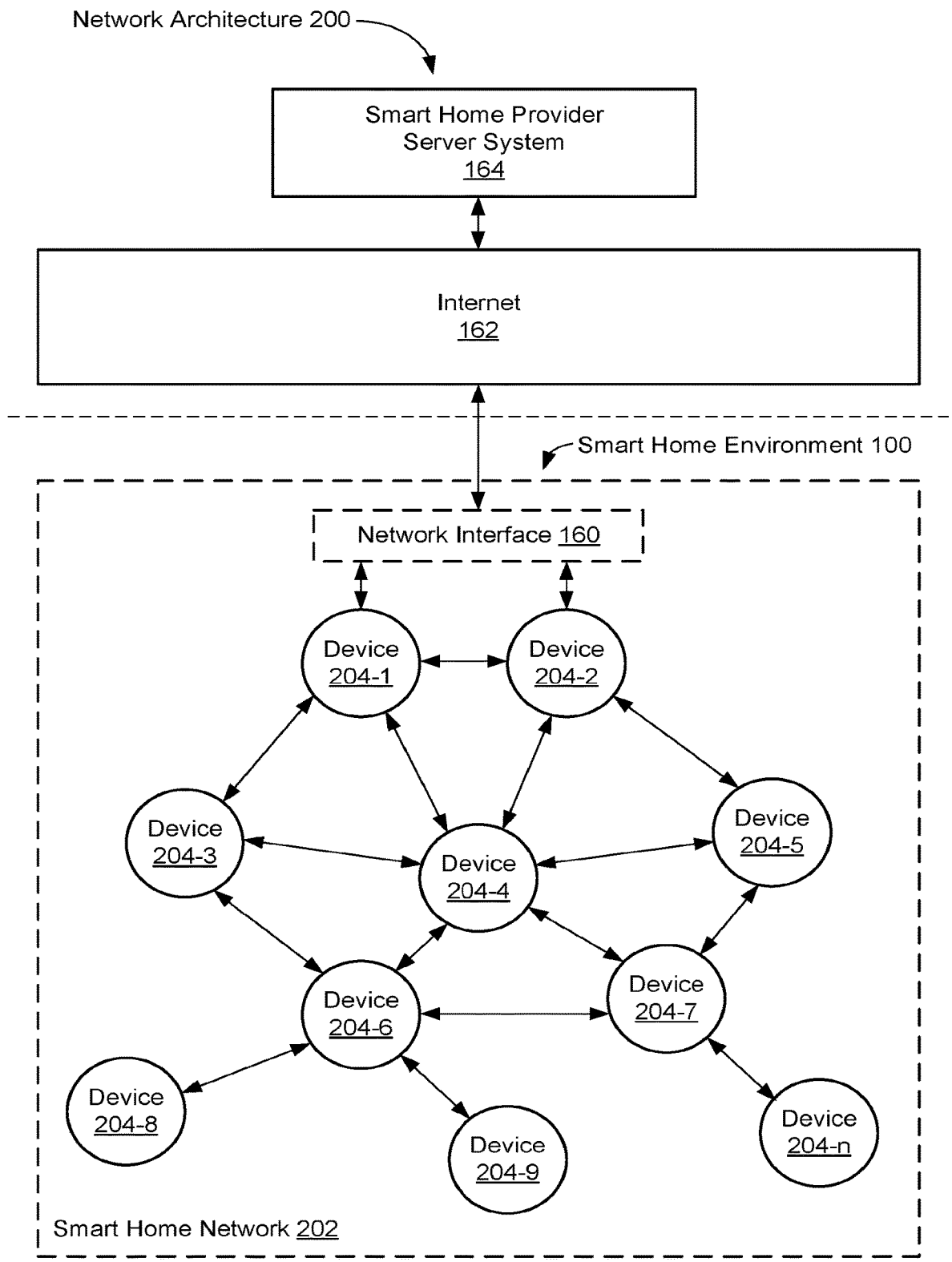
FIG. 2 is a block diagram illustrating an example of a network architecture that includes a smart home network in accordance with some embodiments.

FIG. 2 is a block diagram illustrating an example of a network architecture 200 that includes a smart home network 202 in accordance with some embodiments. In some embodiments, the smart devices 204 in the smart home environment 100 (e.g., devices 102, 104, 106, 108, 110, 112, 114, 116, 118, 170, and/or 172) combine to create a mesh network in smart home network 202. In some embodiments, one or more smart devices 204 in the smart home network 202 operate as a smart home controller. In some embodiments, a smart home controller has more computing power than other smart devices. In some embodiments, a smart home controller processes inputs (e.g., from smart devices 204, electronic device 166, occupancy sensors, occupancy detection devices, and/or smart home provider server system 164) and sends commands (e.g., to smart devices 204 in the smart home network 202) to control operation of the smart home environment 100. In some embodiments, some of the smart devices 204 in the smart home network 202 (e.g., in the mesh network) are "spokesman" nodes (e.g., 204-1) and others are "low-powered" nodes (e.g., 204-9). Some of the smart devices in the smart home environment 100 are battery powered, while others have a regular and reliable power source, such as by connecting to wiring (e.g., to 120V line voltage wires) behind the walls 154 of the smart home environment. The smart devices that have a regular and reliable power source are referred to as "spokesman" nodes. These nodes are typically equipped with the capability of using a wireless protocol to facilitate bidirectional communication with a variety of other devices in the smart home environment 100, as well as with the smart home provider server system 164. In some embodiments, one or more "spokesman" nodes operate as a smart home controller. On the other hand, the devices that are battery powered are the "low-power" nodes. These nodes tend to be smaller than spokesman nodes and typically only communicate using wireless protocols that require very little power, such as Zigbee, 6LoWPAN, etc.

In some embodiments, some low-power nodes are incapable of bidirectional communication. These low-power nodes send messages, but they are unable to "listen". Thus, other devices in the smart home environment 100, such as the spokesman nodes, cannot send information to these low-power nodes.

In some embodiments, some low-power nodes are capable of only a limited bidirectional communication. For example, other devices are able to communicate with the low-power nodes only during a certain time period.

As described, in some embodiments, the smart devices serve as low-power and spokesman nodes to create a mesh network in the smart home environment 100. In some embodiments, individual low-power nodes in the smart home environment regularly send out messages regarding what they are sensing, and the other low-powered nodes in the smart home environment—in addition to sending out their own messages—forward the messages, thereby causing the messages to travel from node to node (i.e., device to device) throughout the smart home network 202. In some embodiments, the spokesman nodes in the smart home network 202, which are able to communicate using a relatively high-power communication protocol, such as IEEE 802.11, are able to switch to a relatively low-power communication protocol, such as IEEE 802.15.4, to receive these messages, translate the messages to other communication protocols, and send the translated messages to other spokesman nodes and/or the smart home provider server system 164 (using, e.g., the relatively high-power communication protocol). Thus, the low-powered nodes using low-power communication protocols are able to send and/or receive messages across the entire smart home network 202, as well as over the Internet 162 to the smart home provider server system 164. In some embodiments, the mesh network enables the smart home provider server system 164 to regularly receive data from most or all of the smart devices in the home, make inferences based on the data, facilitate state synchronization across devices within and outside of the smart home network 202, and send commands back to one or more of the smart devices to perform tasks in the smart home environment.

As described, the spokesman nodes and some of the low-powered nodes are capable of "listening." Accordingly, users, other devices, and/or the smart home provider server system 164 may communicate control commands to the low-powered nodes. For example, a user may use the electronic device 166 (e.g., a smart phone) to send commands over the Internet to the smart home provider server system 164, which then relays the commands to one or more spokesman nodes in the smart home network 202. The spokesman nodes may use a low-power protocol to communicate the commands to the low-power nodes throughout the smart home network 202, as well as to other spokesman nodes that did not receive the commands directly from the smart home provider server system 164.

In some embodiments, a smart nightlight 170 (FIG. 1), which is an example of a smart device 204, is a low-power node. In addition to housing a light source, the smart nightlight 170 houses an occupancy sensor, such as an ultrasonic or passive IR sensor, and an ambient light sensor, such as a photo resistor or a single-pixel sensor that measures light in the room. In some embodiments, the smart nightlight 170 is configured to activate the light source when its ambient light sensor detects that the room is dark and when its occupancy sensor detects that someone is in the room. In other embodiments, the smart nightlight 170 is simply configured to activate the light source when its ambient light sensor detects that the room is dark. Further, in some embodiments, the smart nightlight 170 includes a low-power wireless communication chip (e.g., a ZigBee chip) that regularly sends out messages regarding the occupancy of the room and the amount of light in the room, including instantaneous messages coincident with the occupancy sensor detecting the presence of a person in the room. As mentioned above, these messages may be sent wirelessly (e.g., using the mesh network) from node to node (i.e., smart device to smart device) within the smart home network 202 as well as over the Internet 162 to the smart home provider server system 164.

Other examples of low-power nodes include battery-operated versions of the smart hazard detectors 104. These smart hazard detectors 104 are often located in an area without access to constant and reliable power and may include any number and type of sensors, such as smoke/fire/heat sensors, carbon monoxide/dioxide sensors, occupancy/motion sensors, ambient light sensors, temperature sensors, humidity sensors, and the like. Furthermore, smart hazard detectors 104 may send messages that correspond to each of the respective sensors to the other devices and/or the smart home provider server system 164, such as by using the mesh network as described above.

Examples of spokesman nodes include smart doorbells 106, smart thermostats 102, smart wall switches 108, and smart wall plugs 110. These devices 102, 106, 108, and 110 are often located near and connected to a reliable power source, and therefore may include more power-consuming components, such as one or more communication chips capable of bidirectional communication in a variety of protocols.

In some embodiments, the smart home environment 100 includes service robots 168 (FIG. 1) that are configured to carry out, in an autonomous manner, any of a variety of household tasks.

Figure 3:
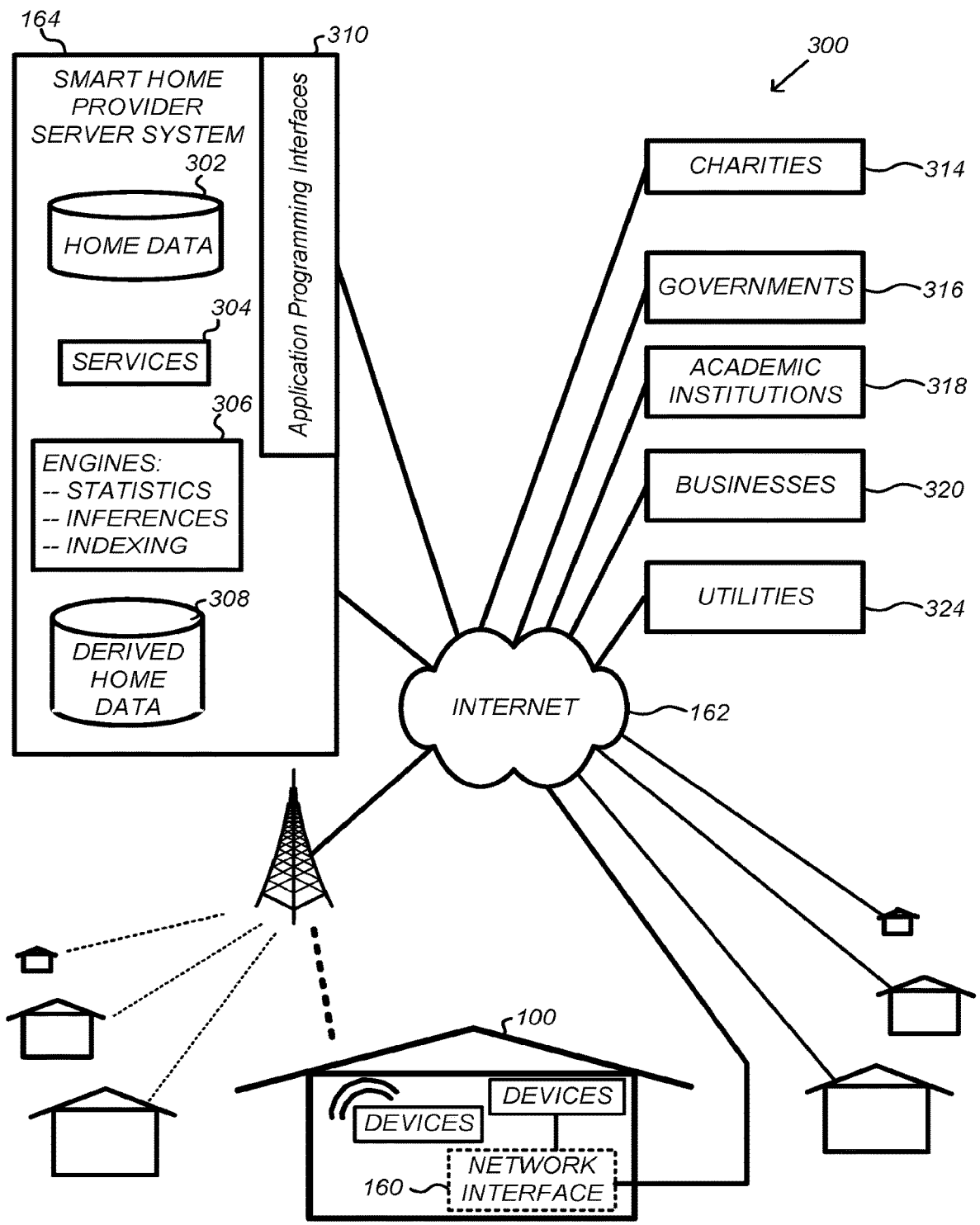
FIG. 3 illustrates a network-level view of an extensible devices and services platform with which the smart home environment of FIG. 1 is integrated, in accordance with some embodiments.

FIG. 3 illustrates a network-level view of an extensible devices and services platform with which the smart home environment of FIG. 1 is integrated, in accordance with some embodiments. The extensible devices and services platform 300 includes smart home provider server system 164. Each of the intelligent, network-connected devices described with reference to FIG. 1 (e.g., 102, 104, 106, 108, 110, 112, 114, 116, 118, 170, and 172, identified simply as "devices" in FIGS. 2-4) may communicate with the smart home provider server system 164. For example, a connection to the Internet 162 may be established either directly (for example, using 3G/4G connectivity to a wireless carrier), or through a network interface 160 (e.g., a router, switch, gateway, hub, or an intelligent, dedicated whole-home controller node), or through any combination thereof.

In some embodiments, the devices and services platform 300 communicates with and collects data from the smart devices of the smart home environment 100. In addition, in some embodiments, the devices and services platform 300 communicates with and collects data from a plurality of smart home environments across the world. For example, the smart home provider server system 164 collects home data 302 from the devices of one or more smart home environments 100, where the devices may routinely transmit home data or may transmit home data in specific instances (e.g., when a device queries the home data 302). Example collected home data 302 includes, without limitation, power consumption data, occupancy data, HVAC settings and usage data, carbon monoxide levels data, carbon dioxide levels data, volatile organic compounds levels data, sleeping schedule data, cooking schedule data, inside and outside temperature humidity data, television viewership data, inside and outside noise level data, pressure data, video data, smart door lock state data, user/occupant location data, etc.

In some embodiments, the smart home provider server system 164 provides one or more services 304 to smart homes and/or third parties. Example services 304 include, without limitation, software updates, customer support, sensor data collection/logging, remote access, remote or distributed control, and/or use suggestions (e.g., based on collected home data 302) to improve performance, reduce utility cost, increase safety, etc. In some embodiments, data associated with the services 304 is stored at the smart home provider server system 164, and the smart home provider server system 164 retrieves and transmits the data at appropriate times (e.g., at regular intervals, upon receiving a request from a user, etc.).

In some embodiments, the extensible devices and services platform 300 includes a processing engine 306, which may be concentrated at a single server or distributed among several different computing entities without limitation. In some embodiments, the processing engine 306 includes engines configured to receive data from the devices of smart home environments 100 (e.g., via the Internet 162 and/or a network interface 160), to index the data, to analyze the data and/or to generate statistics based on the analysis or as part of the analysis. In some embodiments, the analyzed data is stored as derived home data 308.

Results of the analysis or statistics may thereafter be transmitted back to the device that provided home data used to derive the results, to other devices, to a server providing a webpage to a user of the device, or to other non-smart device entities. In some embodiments, use statistics, use statistics relative to use of other devices, use patterns, and/or statistics summarizing sensor readings are generated by the processing engine 306 and transmitted. The results or statistics may be provided via the Internet 162. In this manner, the processing engine 306 may be configured and programmed to derive a variety of useful information from the home data 302. A single server may include one or more processing engines.

The derived home data 308 may be used at different granularities for a variety of useful purposes, ranging from explicit programmed control of the devices on a per-home, per-neighborhood, or per-region basis (for example, demand-response programs for electrical utilities), to the generation of inferential abstractions that may assist on a per-home basis (for example, an inference may be drawn that the homeowner has left for vacation and so security detection equipment may be put on heightened sensitivity), to the generation of statistics and associated inferential abstractions that may be used for government or charitable purposes. For example, processing engine 306 may generate statistics about device usage across a population of devices and send the statistics to device users, service providers or other entities (e.g., entities that have requested the statistics and/or entities that have provided monetary compensation for the statistics).

In some embodiments, to encourage innovation and research and to increase products and services available to users, the devices and services platform 300 exposes a range of application programming interfaces (APIs) 310 to third parties, such as charities 314, governmental entities 316 (e.g., the Food and Drug Administration or the Environmental Protection Agency), academic institutions 318 (e.g., university researchers), businesses 320 (e.g., providing device warranties or service to related equipment, or providing relevant information based on home data), utility companies 324, and other third parties. The APIs 310 are coupled to and permit third-party systems to communicate with the smart home provider server system 164, including the services 304, the processing engine 306, the home data 302, and the derived home data 308. In some embodiments, the APIs 310 allow applications executed by the third parties to initiate specific data processing tasks that are executed by the smart home provider server system 164, as well as to receive dynamic updates to the home data 302 and the derived home data 308.

For example, third parties may develop programs and/or applications, such as web applications or mobile applications, that integrate with the smart home provider server system 164 to provide services and information to users. Such programs and applications may be, for example, designed to help users reduce energy consumption, to pre-emptively service faulty equipment, to prepare for high service demands, to monitor past service performance, etc., and/or to perform other beneficial functions or tasks.

Figure 4:
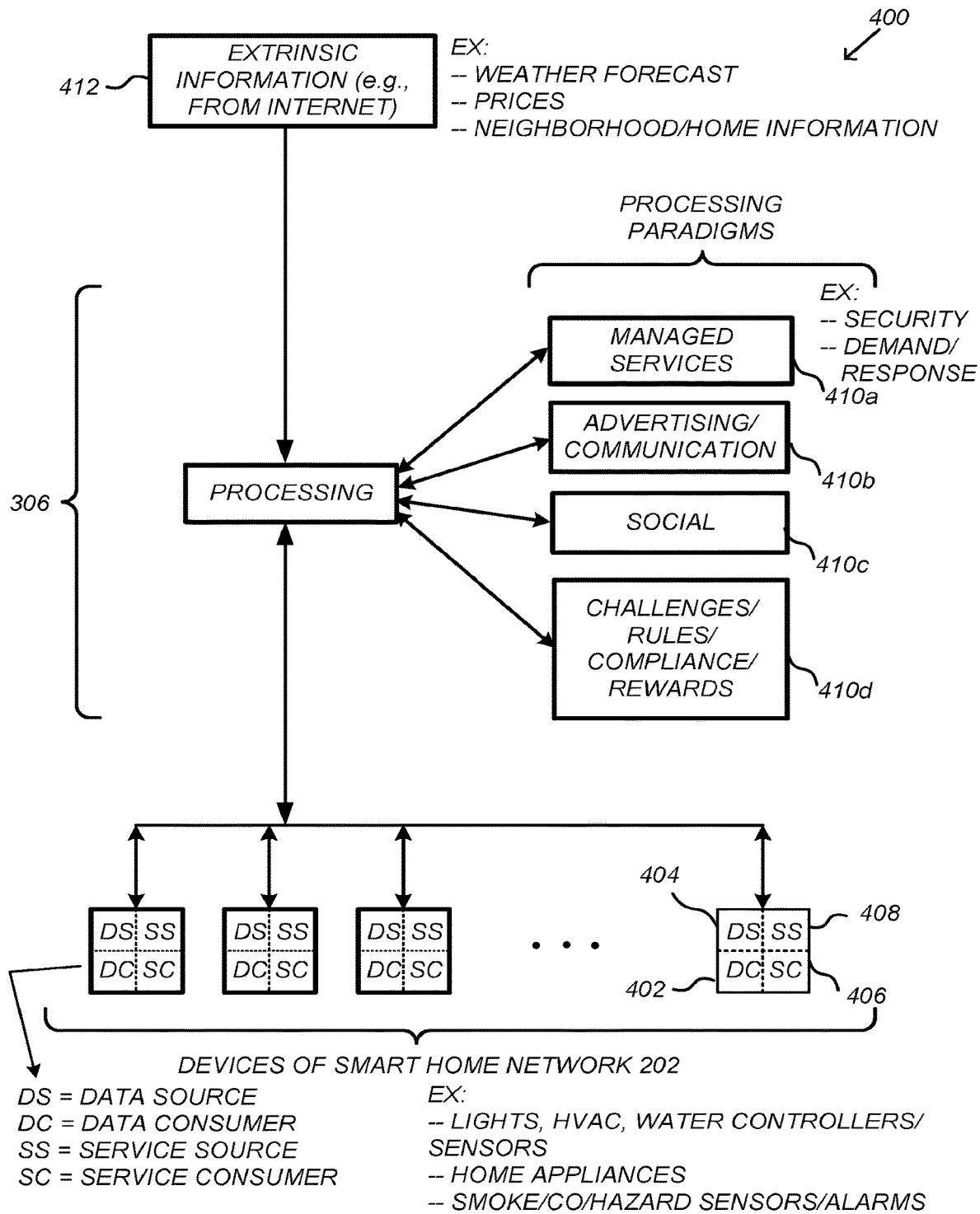
FIG. 4 illustrates an abstracted functional view of the extensible devices and services platform of FIG. 3, with reference to a processing engine as well as devices of the smart home environment, in accordance with some embodiments.

FIG. 4 illustrates an abstracted functional view 400 of the extensible devices and services platform 300 of FIG. 3, with reference to a processing engine 306 as well as devices of the smart home environment, in accordance with some embodiments. Even though devices situated in smart home environments will have a wide variety of different individual capabilities and limitations, the devices may be thought of as sharing common characteristics in that each device is a data consumer 402 (DC), a data source 404 (DS), a services consumer 406 (SC), and a services source 408 (SS). Advantageously, in addition to providing control information used by the devices to achieve their local and immediate objectives, the extensible devices and services platform 300 may also be configured to use the large amount of data that is generated by these devices. In addition to enhancing or optimizing the actual operation of the devices themselves with respect to their immediate functions, the extensible devices and services platform 300 may be directed to "repurpose" that data in a variety of automated, extensible, flexible, and/or scalable ways to achieve a variety of useful objectives. These objectives may be predefined or adaptively identified based on, e.g., usage patterns, device efficiency, and/or user input (e.g., requesting specific functionality).

FIG. 4 shows processing engine 306 as including a number of processing paradigms 410. In some embodiments, processing engine 306 includes a managed services paradigm 410a that monitors and manages primary or secondary device functions. The device functions may include ensuring proper operation of a device given user inputs, estimating that (e.g., and responding to an instance in which) an intruder is or is attempting to be in a dwelling, detecting a failure of equipment coupled to the device (e.g., a light bulb having burned out), implementing or otherwise responding to energy demand response events, enabling or disabling one or more sensors, changing the state of a smart door lock 172, providing a configuration set notification, and/or alerting a user of a current or predicted future event or characteristic. In some embodiments, processing engine 306 includes an advertising/communication paradigm 410b that estimates characteristics (e.g., demographic information), desires and/or products of interest of a user based on device usage. Services, promotions, products or upgrades may then be offered or automatically provided to the user. In some embodiments, processing engine 306 includes a social paradigm 410c that uses information from a social network, provides information to a social network (for example, based on device usage), and/or processes data associated with user and/or device interactions with the social network platform. For example, a user's status as reported to their trusted contacts on the social network may be updated to indicate when the user is home based on light detection, security system inactivation or device usage detectors. As another example, a user may be able to share device-usage statistics with other users. In yet another example, a user may share HVAC settings that result in low power bills and other users may download the HVAC settings to their smart thermostat 102 to reduce their power bills.

In some embodiments, processing engine 306 includes a challenges/rules/compliance/rewards paradigm 410d that informs a user of challenges, competitions, rules, compliance regulations and/or rewards and/or that uses operation data to determine whether a challenge has been met, a rule or regulation has been complied with and/or a reward has been earned. The challenges, rules, and/or regulations may relate to efforts to conserve energy, to live safely (e.g., reducing exposure to toxins or carcinogens), to conserve money and/or equipment life, to improve health, etc. For example, one challenge may involve participants turning down their thermostat by one degree for one week. Those participants that successfully complete the challenge are rewarded, such as with coupons, virtual currency, status, etc. Regarding compliance, an example involves a rental-property owner making a rule that no renters are permitted to access certain owner's rooms. The devices in the room having occupancy sensors may send updates to the owner when the room is accessed.

In some embodiments, processing engine 306 integrates or otherwise uses extrinsic information 412 from extrinsic sources to improve the functioning of one or more processing paradigms. Extrinsic information 412 may be used to interpret data received from a device, to determine a characteristic of the environment near the device (e.g., outside a structure that the device is enclosed in), to determine services or products available to the user, to identify a social network or social-network information, to determine contact information of entities (e.g., public-service entities such as an emergency-response team, the police or a hospital) near the device, to identify statistical or environmental conditions, trends or other information associated with a home or neighborhood, and so forth.

FIG. 5 is a block diagram illustrating an example of a smart device 204 in accordance with some embodiments (e.g., a smart door lock 172). The smart device 204 typically includes one or more processing units (processors or cores) 502, one or more network or other communications interfaces 504, memory 506, and one or more communication buses 508 for interconnecting these components. The communication buses 508 optionally include circuitry (sometimes called a chipset) that interconnects and controls communications between system components. In some embodiments, the smart device 204 includes a user interface 510. The user interface 510 may include a display device 512. In some embodiments, the device 204 includes one or more inputs 516 (e.g., input buttons, a keyboard, a mouse, and/or other input). In some embodiments, the smart device 204 includes a 3D gesture sensor for touchless gesture control. Alternatively or in addition, in some embodiments, the display device 512 includes a touch-sensitive surface 514, in which case the display device 512 is a touch-sensitive display. In some embodiments, the user interface 510 also includes an audio output device 518, such as speakers or an audio output connection connected to speakers, earphones, or headphones. Furthermore, some smart devices 204 use a microphone and voice recognition to supplement or replace the keyboard. Optionally, the smart device 204 includes an audio input device 520 (e.g., a microphone) to capture audio (e.g., speech from a user, sounds caused by one or more occupants). Optionally, the smart device 204 includes a location detection device 521, such as a GPS (Global Positioning System), BLE (Bluetooth Low Energy), or other geo-location receiver, for determining the location of the smart device 204. The smart device 204 also optionally includes an image/video capture device 524 (e.g., a camera 118), which may serve as an occupancy sensor.

In some embodiments, the smart device 204 includes one or more motion sensors 522 (e.g., a passive infrared sensor) that detect motion by one or more occupants. In some embodiments, the smart device 204 includes one or more ambient light sensors 525 that measure the ambient light at the location of the smart device 204. In some embodiments, the smart device 204 includes one or more touch sensors 554 (e.g., a touch-sensitive surface separate from the touch-sensitive surface 514 associated with the display 512) to detect touch and/or pressure made by occupants (e.g., with the occupants' hands). In some embodiments, the smart device 204 includes other occupancy sensors in addition to or as an alternative to the image/video capture device 524, motion sensor 522, ambient light sensor 525, audio input device 520, and/or touch sensor 554.

If the smart device 204 is a smart door lock 172, in some embodiments, the smart door lock 172 includes a lock sensor 552 that detects the state of the smart door lock 172, i.e. whether the smart door lock 172 is in the locked state or the unlocked state. In some embodiments, the lock sensor 552 detects whether the smart door lock 172 was locked or unlocked from the inside or the outside with respect to the room 152 or structure 150 with which the smart door lock 172 is associated.

Memory 506 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 506 may optionally include one or more storage devices remotely located from the processor(s) 502. Memory 506, or alternately the non-volatile memory device(s) within memory 506, includes a non-transitory computer readable storage medium. In some embodiments, memory 506 or the computer readable storage medium of memory 506 stores the following programs, modules and data structures, or a subset or superset thereof:

- an operating system 526 that includes procedures for handling various basic system services and for performing hardware dependent tasks;
- a network communication module 528 that is used for connecting the smart device 204 to other computers via the one or more communication network interfaces 504 (wired or wireless) and one or more communication networks, such as smart home network 202 (e.g., a mesh network), the Internet, cellular telephone networks, mobile data networks, other wide area networks, local area networks, metropolitan area networks, and so on;
- an image/video capture module 530 (e.g., a camera module) for processing a respective image or video captured by the image/video capture device 524, where the respective image or video may be sent or streamed (e.g., by a client application module 540) to the smart home network 202 and/or smart home provider server system 164;
- an audio input module 532 (e.g., a microphone module) for processing audio captured by the audio input device 520, where the respective audio may be sent or streamed (e.g., by a client application module 540) to the smart home network 202 and/or smart home provider server system 164;
- a motion data module 534 for processing motion data (e.g., passive infrared data) captured by the motion sensor 522, where the data may be sent or streamed through the smart home network 202 to a portable electronic device 166, smart home provider server system 164, other smart device 204, and/or other computing system;
- an occupancy data module 536 for processing data captured by the image/video capture device 524, audio input device 520, motion sensor 522, ambient light sensor 525, lock sensor 552, and/or other occupancy sensors, where the data may be sent or streamed through the smart home network 202 to a portable electronic device 166, smart home provider server system 164, other smart device 204, and/or other computing system;
- an ambient light data module 537 for processing data captured by the ambient light sensor 525, where the data may be sent or streamed through the smart home network 202 to a portable electronic device 166, smart home provider server system 164, other smart device 204, and/or other computing system;
- a location detection module 538 (e.g., a GPS, Wi-Fi, or hybrid positioning module) for determining the location of the smart device 204 (e.g., using the location detection device 522) and providing this location information to the smart home network 202 and/or smart home provider server system 164;
- a touch data module 556 for processing data captured by the touch sensor 554, where the data may be sent or streamed through the smart home network 202 to a portable electronic device 166, smart home provider server system 164, other smart device 204, and/or other computing system;
- a lock data module 558 for processing data captured by the lock sensor 552, where the data may be sent or streamed through the smart home network 202 to a portable electronic device 166, smart home provider server system 164, other smart device 204, and/or other computing system; and
- one or more application modules 540, including the following modules (or sets of instructions), or a subset or superset thereof:
  - a smart home module 542 for providing an interface to a smart home application (e.g., a stand-alone application or an application in communication with another device in smart home network 202 and/or smart home provider server system 164) and related features;
  - an occupancy-determination module 544 for determining occupancy of a room in the structure 150 in which the smart device 204 is located, and/or respective rooms 152 of the structure 150 (e.g., based on occupancy data received from the image/video capture device 524, audio input device 520, motion sensor 522, ambient light sensor 525, touch sensor 554, lock sensor 552, and/or other occupancy sensors, and/or other smart devices 204 in different rooms 152);

a configuration module 546 to set the smart home environment 100 to any one of multiple configurations, automatically based on various parameters including occupancy (e.g., as determined by the occupancy-determination module 544), location of a user, and data of a smart door lock 172 (e.g., from lock sensor 552), and/or manually based on a user command;

a configuration notification module 548 to send notifications to a user when a configuration of the smart home environment 100 changes; and/or configuration data 550 to store data corresponding to respective configurations (e.g., a first configuration 550-1, a second configuration 550-2, and so on), including which respective configuration is the currently set configuration, criteria or thresholds for activating a respective configuration, and settings and operations associated with a respective configuration (e.g., enabling or disabling particular sensors or smart devices 204, locking or unlocking particular smart door locks 172, sending a notification, etc.).

It should be appreciated that, depending on the particular smart device 204, one or more of the components or modules described above may be omitted from the smart device 204. For example, a smart device 204 that is not a smart door lock 172 may omit the lock sensor 552 and the lock data module 558.

FIG. 6 is a block diagram illustrating an example of a computing system 600 in accordance with some embodiments. In some embodiments, the computing system 600 is a computer or other portable electronic device 166. In some embodiments, the computing system 600 is the smart home provider server system 164 or another server system outside of the structure 150. In some embodiments, the computing system 600 is a stand-alone controller (e.g., located in the structure 150) that is distinct from the smart devices 204 and the smart home provider server system 164. In some embodiments, the computing system 600 is a smart device 204 (e.g., with additional components as shown in FIG. 5) or a collection of multiple smart devices 204. For example, the computing system 600 may have a housing that contains the components shown in FIG. 6 and also contains a smart door lock 172, and/or at least one occupancy sensor (e.g., a camera 118, audio input device 520, motion sensor 522, ambient light sensor 525, touch sensor 554, lock sensor 552, or other occupancy sensor). For example, the computing system 600, a motion sensor, and a smart door lock 172 are contained in a single enclosure.

The computing system 600 typically includes one or more processing units (processors or cores) 602, one or more network or other communications interfaces 604, memory 606, and one or more communication buses 608 for interconnecting these components. The communication buses 608 optionally include circuitry (sometimes called a chipset) that interconnects and controls communications between system components. In some embodiments, the computing system 600 includes a user interface 605 (e.g., which is analogous to the user interface 510, FIG. 5).

Memory 606 includes high-speed random access memory, such as DRAM, SRAM, DDR RAM or other random access solid state memory devices; and may include non-volatile memory, such as one or more magnetic disk storage devices, optical disk storage devices, flash memory devices, or other non-volatile solid state storage devices. Memory 606 may optionally include one or more storage devices remotely located from the processor(s) 602. Memory 606, or alternately the non-volatile memory device(s) within memory 606, includes a non-transitory computer readable storage medium. In some embodiments, memory 606 or the computer readable storage medium of memory 606 stores the following programs, modules and data structures, or a subset or superset thereof:

an operating system 610 that includes procedures for handling various basic system services and for performing hardware-dependent tasks;

a network communication module 612 that is used for connecting the computing system 600 to other computers via the one or more communication network interfaces 604 (wired or wireless) and one or more communication networks, such as smart home network 202 (e.g., a mesh network), the Internet 162, cellular telephone networks, mobile data networks, other wide area networks, local area networks, metropolitan area networks, and so on;

a database 614 that includes the following data:
  occupancy information 615 (e.g., received from occupancy data modules 536 in respective devices 204, FIG. 5);
  motion information 616 (e.g., received from motion data modules 534 in respective devices 204, FIG. 5);
  ambient light information 617 (e.g., received from ambient light modules 537 in respective devices 204, FIG. 5);
  image/video information 618 (e.g., received from image/video capture modules 530 in respective smart devices 204, FIG. 5);
  audio information 619 (e.g., received from audio input modules 532 in respective smart devices 204, FIG. 5);
  touch information 620 (e.g., received from touch data modules 556 in respective smart devices 204, FIG. 5); and/or
  lock information 621 (e.g., received from lock data modules in respective smart devices 204, FIG. 5);

one or more application modules 622, including the following modules (or sets of instructions), or a subset or superset thereof:
  an occupancy-determination module 624 for determining occupancy of the structure 150 and/or respective rooms 152 of the structure 150 (e.g., based on the occupancy information 615, motion information 616, ambient light information 617, image/video information 618, audio information 619, touch information 620, and/or lock information 621 in the database 614);
  a configuration module 626 to set the smart home environment 100 to any one of multiple configurations, automatically based on various parameters including occupancy (e.g., as determined by the occupancy-determination module 544), location of a user, and data of a smart door lock 172 (e.g., from lock sensor 552), and/or manually based on a user command;

a configuration notification module 628 to send notifications to a user when a configuration of the smart home environment 100; and/or configuration data 630 to store data corresponding to respective configurations (e.g., a first configuration 630-1, a second configuration 630-2, and so on), including which respective configuration is the currently set configuration, criteria or thresholds for activating a respective configuration, and settings and operations associated with a respective configuration (e.g., enabling or disabling particular sensors or smart devices 204, locking or unlocking particular smart door locks 172, sending a notification, etc.).

In some embodiments, the computer system 600 includes one or more of: image capture device 524, audio input device 520, motion sensor 522, ambient light sensor 525, touch sensor 554, lock sensor 552, and/or other occupancy sensors and their respective corresponding modules (e.g., image/video capture module 530, audio input module 532, motion data module 534, ambient light data module 537, touch data module 556, and lock data module 558, respectively) and/or occupancy data module 536.

Each of the above identified modules and applications of FIGS. 5-6 corresponds to a set of executable instructions for performing one or more functions described above and the methods described in this application (e.g., the computer-implemented methods and other information processing methods described herein). These modules (i.e., sets of instructions) need not be implemented as separate software programs, procedures or modules, and thus various subsets of these modules are, optionally, combined or otherwise re-arranged in various embodiments. In some embodiments, memory 506 and/or 606 store a subset of the modules and data structures identified above. Furthermore, memory 506 and/or 606 optionally store additional modules and data structures not described above.

Attention is now directed towards embodiments of graphical user interfaces ("UI") and associated processes that may be implemented on an electronic device to present notifications that a configuration has been set, and allow a user to respond to configuration set notifications (e.g., by manually setting a different configuration).

FIG. 7 illustrates an example of a GUI 704 displayed on a screen 702 of a portable electronic device 166 (or other computing system, such as a smart device 204) in accordance with some embodiments. The GUI 704 illustrates aspects of operations in the methods 800 (FIGS. 8A-8B) and 900 (FIGS. 9A-9C). In some embodiments, the screen 702 is an example of a user interface 605 (FIG. 6). In some embodiments, the screen 702 is an example of a display 512 (FIG. 5) of a smart device 204. In some embodiments, the GUI 704 is generated based on information from a computing system 600 (FIG. 6).

The GUI 704 displays a configuration notification 706, which in this example indicates that the home controller (i.e., a controller device for the smart home environment 100) has been set to a particular configuration, among multiple configurations, named "Away+Secure." The GUI 704 also presents user-interface elements 708 and/or 710 that allow the user to acknowledge and dismiss the configuration notification 706 and/or to activate a user interface to manually set a configuration. Selection of the element 708 (e.g., through an appropriate gesture on the screen 702, such as a tap) dismisses the configuration notification 706 and indicates that the user acknowledges the setting of the configuration. Selection of the element 710 dismisses the configuration notification 706 and activates a user interface (not shown) for manually setting a configuration of the home controller, thus giving the user an opportunity to override the setting of the configuration as indicated by the notification 706 by setting another configuration.

Figure 8A:
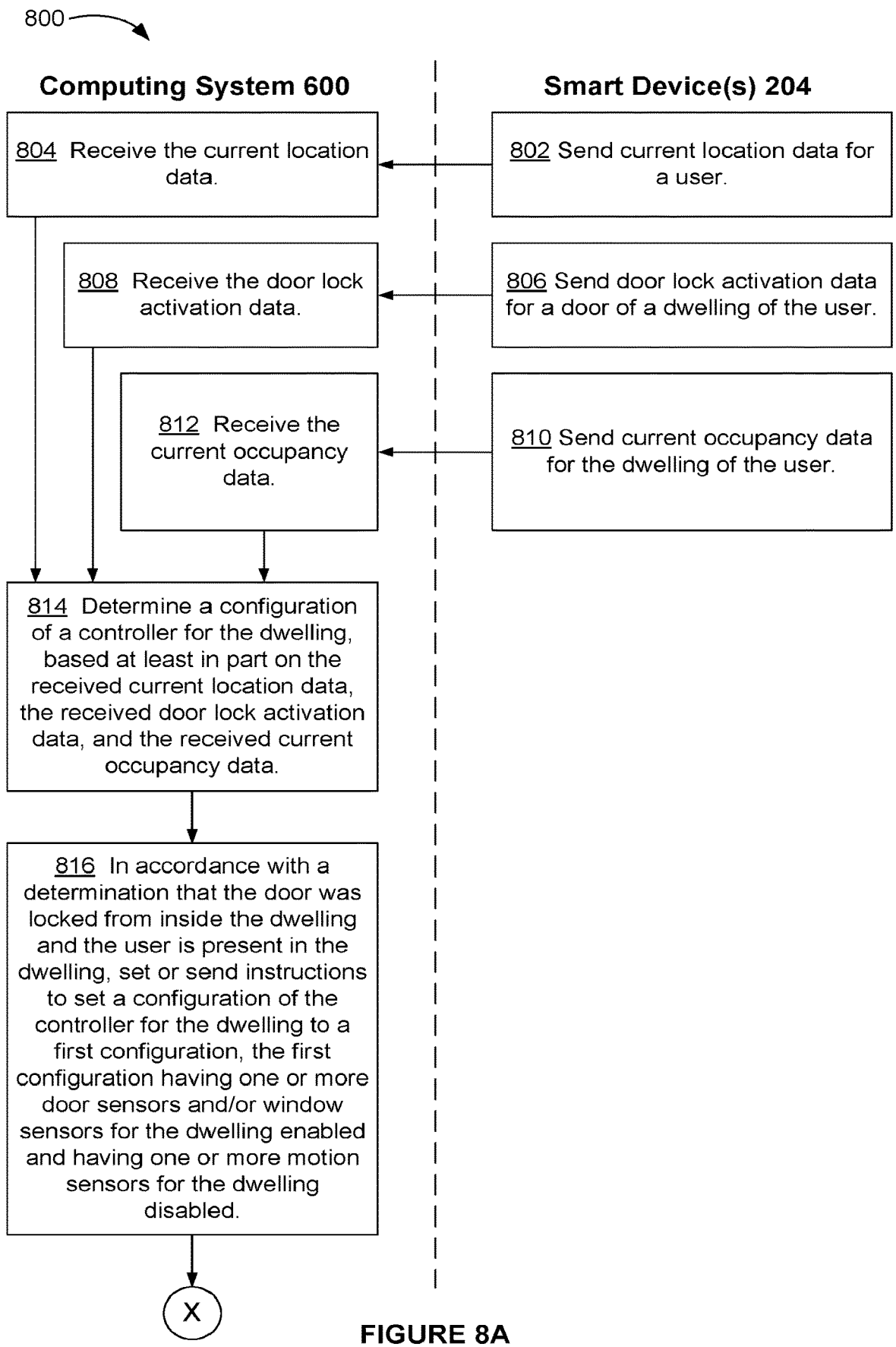
Figure 8B:
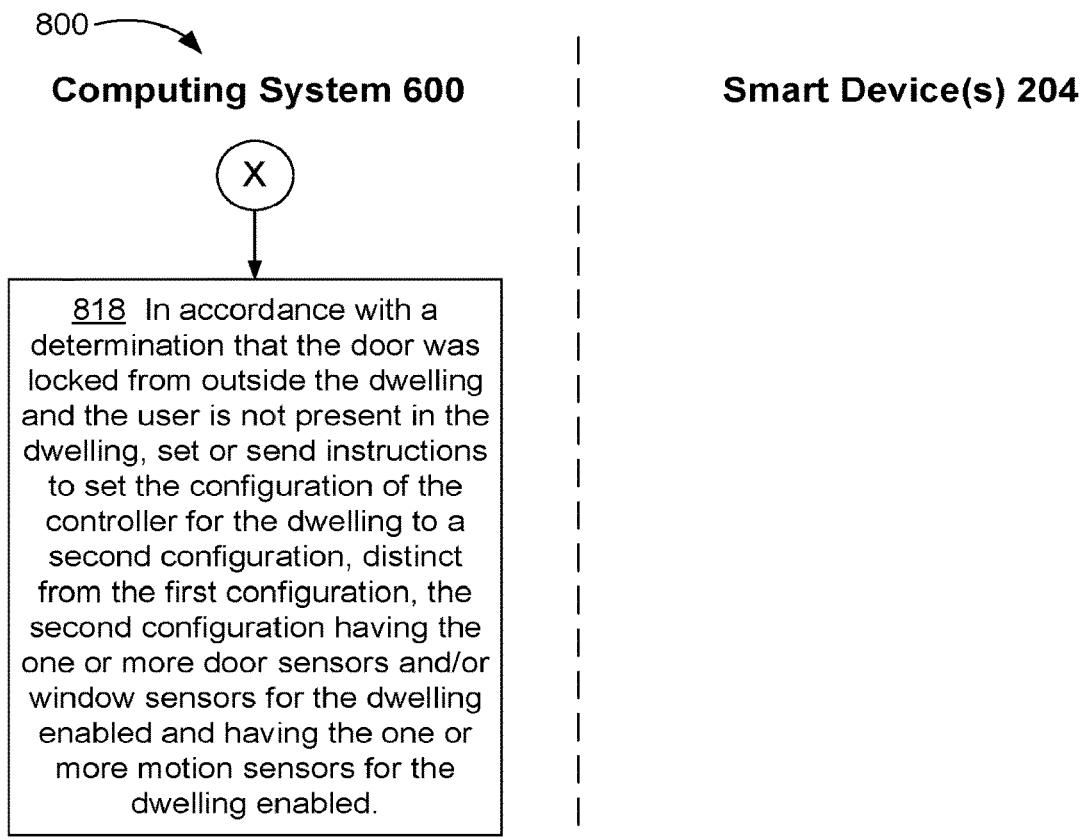
Figure 9A:
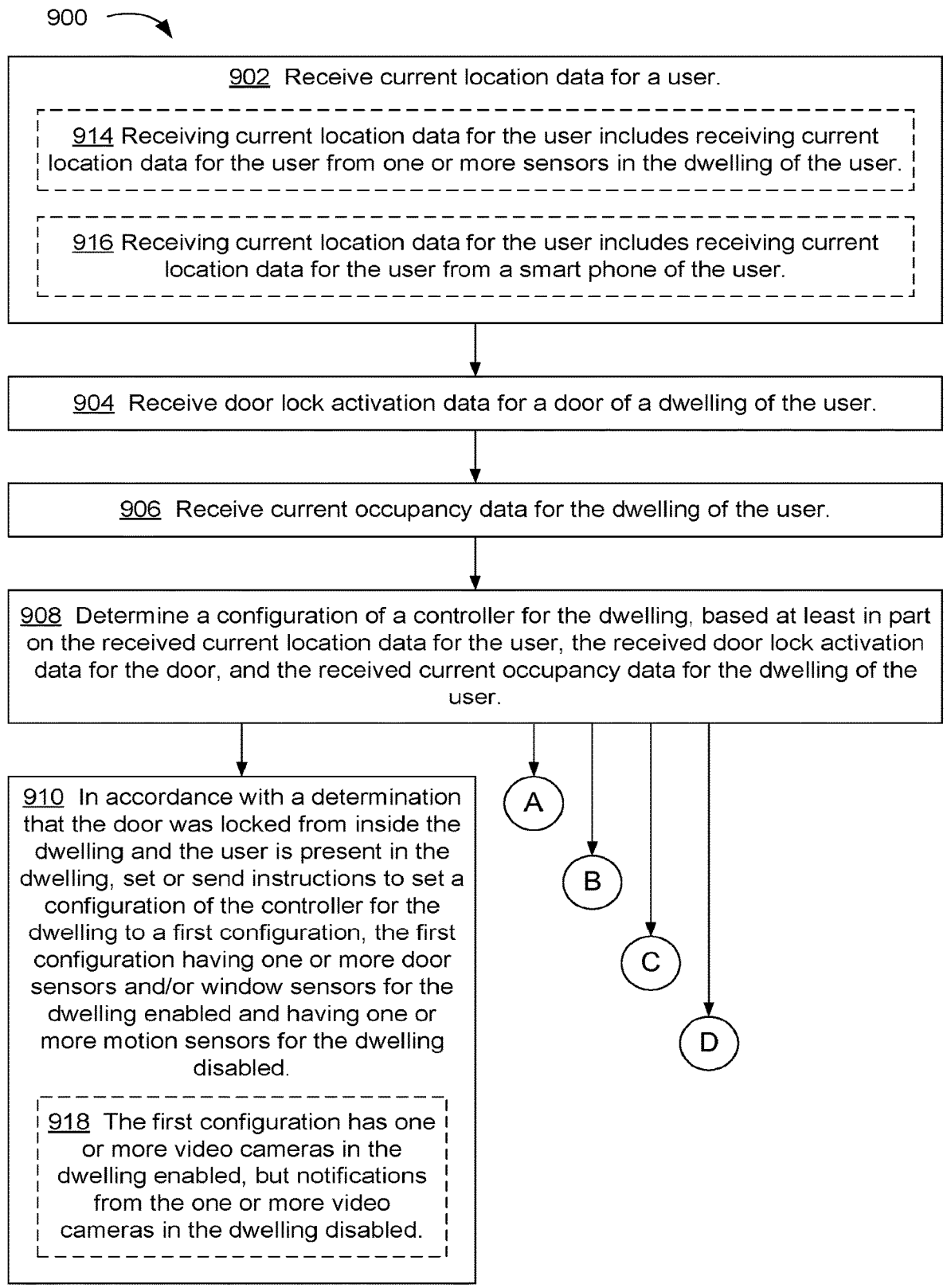
Figure 9C:

FIGS. 8A-8B are flow diagrams illustrating a method 800 of setting a configuration of a smart home controller in accordance with some embodiments. Respective portions of the method 800 are performed by smart devices 204 (FIGS. 2, 5) and a computing system 600 (FIG. 6). The method 800 corresponds to instructions stored in one or more non-transitory computer-readable storage media. For example, the portions performed by smart devices 204 correspond to instructions stored in memory 506 (FIG. 5) and the portions performed by the computing system 600 correspond to instructions stored in the memory 606 (FIG. 6). Examples and details of the portion of the method 800 performed by the computing system 600 are provided below in the method 900 (FIGS. 9A-9C).

One or more location devices (e.g., location detection device 521, camera 118) send (802) current location data for a user. The computing system 600 receives (804) this data. In some embodiments, the computing system determines a current location of the user with this data, and optionally determines whether the user's current location is within a predefined distance from the smart home environment 100 (e.g., within a geo-fence).

One or more smart door lock 172 sends (806) door lock activation data for respective doors (with which the smart door locks 172 are respectively associated) of a dwelling of the user. The computing system 600 receives (808) this data. In some embodiments, the computing system determines respective lock states (e.g., locked or unlocked, whether the lock was operated from the inside or the outside) for the doors with this data.

One or more occupancy sensors (e.g., cameras 118, audio input device 520, motion sensor 522, ambient light sensor 525, touch sensor 554, lock sensors 552, and/or other occupancy sensors) send (810) current occupancy data for the dwelling of the user. The computing system 600 receives (812) this data. In some embodiments, the computing system determines an occupancy of the dwelling with this data.

The computing system 600 determines (814) a configuration of a controller for the dwelling, based at least in part on the received current location data for the user, the received door lock activation data for the door(s), and received current occupancy data for the dwelling of the user. In some embodiments, different combinations of user location, lock state, and/or occupancy (and optionally additional parameters) are associated with respective configurations. A respective configuration may be associated with multiple different combinations of user location, lock state, and occupancy.

In accordance with a determination that the door was locked from inside the dwelling and the user is present in the dwelling, the computer system 600 sets or sends instructions to set (816) a configuration of the controller for the dwelling to a first configuration. The first configuration has one or more door sensors and/or window sensors for the dwelling enabled and having one or more motion sensors for the dwelling disabled.

In accordance with a determination that the door was locked from outside the dwelling and the user is not present in the dwelling, the computer system 600 sets or sends instructions to set (818) the configuration of the controller for the dwelling to a second configuration distinct from the first configuration. The second configuration has the one or more door sensors and/or window sensors for the dwelling enabled and having the one or more motion sensors for the dwelling enabled.

In some embodiments, other operations are performed in addition to setting or sending instructions to set the configuration. For example, a notification that a configuration is set (e.g., notification 706, FIG. 7) may be sent to the user. As another example, for particular combinations of user location, lock state, and/or occupancy, the computer system 600 may lock or send instructions to lock or unlock one or more doors in addition to setting the configuration.

FIGS. 9A-9C are flow diagrams illustrating a method 900 of setting a configuration of a smart home controller in accordance with some embodiments. The method 900 is performed by a computing system 600 (FIG. 6) and corresponds to instructions stored in a non-transitory computer-readable storage medium (e.g., memory 606, FIG. 6).

The computer system 600 receives (902) current location data for a user (e.g., from a smart phone 166 being carried by the user, from one or more video cameras in the user's dwelling, and/or from a video camera outside the dwelling that is directed towards the door). In some embodiments, the computer system 600 determines a current location for the user using this received data.

The computer system 600 receives (904) door lock activation data for a door of a dwelling of the user (e.g., receiving, from a smart door lock, data indicating that the door lock in the door has changed from an unlocked state to a locked state). For example, the smart door lock 172 for a door leading to the outside of the structure 150 sends its activation data (e.g., its lock state data, whether the lock was operated from the inside or the outside) to the computer system 600.

The computer system 600 receives (906) current occupancy data for the dwelling of the user (e.g., from one or more video cameras in the user's dwelling, and/or from one or more motion sensors in the dwelling). The dwelling (e.g., structure 150) includes one or more sensors for detecting occupancy (e.g., camera 118, audio input device 520, motion sensor 522, etc.) on one or more smart devices 204. In some embodiments, the occupancy module 624 determines an occupancy of the dwelling based on the received occupancy data.

The computer system 600 determines (908) a configuration of a controller for the dwelling, based at least in part on the received current location data for the user, the received door lock activation data for the door, and the received current occupancy data for the dwelling of the user. For example, the configuration module 626 determines a configuration based on the location of the user, the lock state of one or more doors of the dwelling (e.g., structure 150), and the occupancy of the dwelling (e.g., as determined by occupancy determination module 624).

In accordance with a determination that the door was locked from inside the dwelling (e.g., based on detected inputs on touch-sensitive surfaces connected to the door lock, motion sensors on or near the door, and/or video from cameras trained on the inside of the door) and the user is present in the dwelling (e.g., from a smart phone being carried by the user and/or from one or more video cameras in the user's dwelling), the computer system 600 sets or sends instructions to set (910) a configuration of the controller for the dwelling (e.g., setting a mode or state of the smart home controller) to a first configuration. The first configuration has one or more door sensors and/or window sensors for the dwelling enabled and has one or more motion sensors for the dwelling disabled (e.g., a "Home+Secure" configuration that arms sensors on outer doors and windows of the dwelling, but which turns off motion sensors within the dwelling). If the user is in the structure 152 and the smart door lock 172 for the main door was locked from the inside (which indicates that the user is inside the structure), the configuration module 626 sets the controller to a first configuration and enables/disables respective sensors in accordance with the first configuration. In the first configuration, the door and/or window sensors in the structure 150 are enabled, but the motion sensors in the structure 150 are disabled to prevent false alarms being triggered by the user moving within the dwelling.

In accordance with a determination that the door was locked from outside the dwelling and the user is not present in the dwelling, the computer system 600 sets or sends instructions to set (912) the configuration of the controller for the dwelling to a second configuration distinct from the first configuration. The second configuration has the one or more door sensors and/or window sensors for the dwelling enabled and has the one or more motion sensors for the dwelling enabled (e.g., a "Away+Secure" configuration that arms sensors on outer doors and windows of the dwelling, and which also turns on motion sensors within the dwelling). If the user is not in the structure 152 and the smart door lock 172 for the main door was locked from the outside (which implies that the user is outside the structure), the configuration module 626 sets the controller to a second configuration different from the first configuration and enables/disables respective sensors in accordance with the second configuration. In the second configuration, the door and/or window sensors and the motion sensors in the structure 150 are enabled.

In some embodiments, a notification is sent to the user whenever a respective configuration is set for controller. For example, FIG. 7 illustrates a notification sent to inform the user that the controller has been set to the "Away+Secure" configuration.

Thus, the proper configuration of the smart home controller can be set in response to a user locking a door (e.g., a front door of the dwelling or a door to a garage in the dwelling) and staying or going, without the user needing to explicitly request a particular configuration. For example, the user does not need to input a request for a particular configuration via a keypad for the smart home controller or via a smart home application on a smart phone.

In some embodiments, receiving current location data for the user includes receiving (914) current location data for the user from one or more sensors in the dwelling of the user. For example, the computer system 600 receives the location data from one or more sensors (e.g., audio input device 520, motion sensor 522, etc.) in the structure 150.

In some embodiments, receiving current location data for the user includes receiving (916) current location data for the user from a smart phone of the user. For example, the computer system 600 receives the location data from a device 166 associated with the user.

In some embodiments, the first configuration has (918) one or more video cameras in the dwelling enabled, but notifications from the one or more video cameras in the dwelling disabled (and HVAC in the dwelling turned on to a currently scheduled set point for an at-home schedule). For example, when the user is in the structure 150 and the structure 150 is locked from the inside, video cameras are enabled, so they continue monitoring the structure 150, but notifications from the video cameras are disabled, as the notifications are likely to be notifications about the user in the structure 150, and thus not needed by the user. Also, the HVAC in the structure 150 may be set for an occupied structure.

In some embodiments, the second configuration has (920) one or more video cameras in the dwelling enabled, and notifications from the one or more video cameras in the dwelling enabled (and HVAC in the dwelling turned on to a currently scheduled set point for an away schedule). For example, when the user is not in the structure 150 and the structure 150 is locked from the outside, video cameras are enabled, so they continue monitoring the structure 150, and notifications from the video cameras are enabled, so that the user is notified about suspicious activity in the structure 150. Also, the HVAC in the structure 150 may be set for an unoccupied structure.

In some embodiments, in accordance with a determination that the door was locked from inside the dwelling, the user is not present in the dwelling, and the dwelling is unoccupied, the computer system 600 sets or sends instructions to set (922) the configuration of the controller for the dwelling to the second configuration. For example, the computer system 600 sets the controller to the "Away+Secure" configuration if the door (and by implication, the structure 150) was locked from the inside, the user is not in the structure 150, and the structure 150 is unoccupied.

In some embodiments, in accordance with a determination that the door is unlocked, the user is not present within a geo-fence around the dwelling, and the dwelling is unoccupied, the computer system 600 sets or sends instructions to set (924) the configuration of the controller for the dwelling to the second configuration, and locks or sends instructions to lock one or more doors in the dwelling. For example, the computer system 600 sets the controller to the "Away+Secure" configuration if the door (and by implication, the structure 150) is unlocked, the user is not within a predefined distance from the structure 150, and the structure 150 is unoccupied. In addition, the computer system 600 also locks one or more smart door locks 172 in the structure 150 or sends instructions to do the same.

In some embodiments, in accordance with a determination that the door is unlocked, the user is not present within a geo-fence around the dwelling, and the dwelling is unoccupied, the computer system 600 sets or sends instructions to set (926) the configuration of the controller for the dwelling to the second configuration, locks or sends instructions to lock one or more doors in the dwelling, and sends a notification to the user that the controller has been placed in the second configuration. For example, the computer system 600 sets the controller to the "Away+Secure" configuration if the door (and by implication, the structure 150) is unlocked, the user is not within a predefined distance from the structure 150, and the structure 150 is unoccupied. In addition, the computer system 600 also locks one or more smart door locks 172 in the structure 150 or sends instructions to do the same, and sends a notification to the user informing the user that the "Away+Secure" configuration has been set and one or more smart door locks 172 have been locked.

It should be appreciated that the configurations above, the combinations of parameters (e.g., user location, lock state, occupancy, etc.) that result in respective configurations being set, and operations (e.g., enable/disable sensors, lock/unlock doors, send notification, etc.) associated with a respective configuration and/or a combination of parameters are merely examples. Other configurations in addition to those described above, other combinations of parameters in addition to those described above, and other operations are possible.

In some embodiments, a housing that contains the computer system also contains a door lock for the door (928). For example, the computer system 600 and the smart door lock 172 for the main door of the structure 150 are contained in the same housing.

In some embodiments, the computer system is the smart home controller (930). For example, the computer system 600 also serves as the smart home controller.

In some embodiments, the computer system is located in a smart home provider server system remote from the dwelling (932). For example, the computer system 600 is located at the smart home provider server system 164.

For situations in which the systems discussed above collect information about users, the users may be provided with an opportunity to opt in/out of programs or features that may collect personal information (e.g., information about a user's preferences or usage of a smart device). In addition, in some embodiments, certain data may be anonymized in one or more ways before it is stored or used, so that personally identifiable information is removed. For example, a user's identity may be anonymized so that the personally identifiable information cannot be determined for or associated with the user, and so that user preferences or user interactions are generalized (for example, generalized based on user demographics) rather than associated with a particular user.

Although some of various drawings illustrate a number of logical stages in a particular order, stages that are not order dependent may be reordered and other stages may be combined or broken out. While some reordering or other groupings are specifically mentioned, others will be obvious to those of ordinary skill in the art, so the ordering and groupings presented herein are not an exhaustive list of alternatives. Moreover, it should be recognized that the stages could be implemented in hardware, firmware, software or any combination thereof.

The foregoing description, for purpose of explanation, has been described with reference to specific embodiments. However, the illustrative discussions above are not intended to be exhaustive or to limit the scope of the claims to the precise forms disclosed. Many modifications and variations are possible in view of the above teachings. The embodiments were chosen in order to best explain the principles underlying the claims and their practical applications, to thereby enable others skilled in the art to best use the embodiments with various modifications as are suited to the particular uses contemplated.

The invention claimed is:

1. A method, comprising:
receiving, by a smart home provider server system from a smart home controller, location data for the smart home controller being controlled by a user;
receiving, by the smart home provider server system from the smart home controller, door lock activation data;
setting, by the smart home provider server system, a configuration of the smart home controller for a dwelling to a first configuration based at least in part on a determination that a door was locked from inside the dwelling based on the location data from the smart home controller being controlled by the user, wherein the first configuration comprises disabling transmission to the smart home controller of notifications generated based on data from a sensor while the sensor continues to monitor at least a portion of the dwelling; and setting, by the smart home provider server system, the configuration of the smart home controller to a second configuration from the first configuration based at least in part on a determination that the door was locked from outside the dwelling based on the location data from the smart home controller being controlled by the user, wherein:

the second configuration comprises enabling transmission to the smart home controller of notifications from the smart home provider server system based on data generated by the sensor.

2. The method of claim 1, further comprising:

in response to sending a notification to a user, receiving a user request to set the smart home controller to a third configuration; and in response to receiving the user request, setting or sending instructions to set the smart home controller to the third configuration.

3. The method of claim 1, wherein the sensor coupled to the smart home controller includes a motion sensor for the dwelling, wherein the first configuration has the motion sensor disabled, and wherein the second configuration has the motion sensor enabled.

4. The method of claim 1, wherein the first configuration comprises a user-home configuration, and wherein the second configuration comprises a user-away configuration.

5. The method of claim 1, wherein setting or sending instructions to set the configuration of the smart home controller to the second configuration includes:

determining whether the door of the dwelling is locked based on the obtained door lock activation data; and in accordance with a determination that the door of the dwelling is unlocked, locking or sending instructions to lock the door.

6. The method of claim 1, further comprising:

obtaining current occupancy data for the dwelling of the user;

determining whether the dwelling is currently occupied based at least in part on the obtained current occupancy data; and while operating in the first configuration, setting or sending instructions to set the configuration of the smart home controller to the second configuration based on a determination that the dwelling is unoccupied.

7. The method of claim 6, wherein obtaining the current occupancy data for the dwelling of the user includes receiving current location data for the user from (i) a smart phone of the user, and/or (ii) one or more sensors in the dwelling of the user.

8. The method of claim 6, wherein the current occupancy data includes two or more of: motion data, visual data, audio data, ambient light data, touch data, ultrasonic data, and passive infrared data.

9. The method of claim 6, further comprising: identifying one or more occupants in the dwelling based on the obtained occupancy data.

10. The method of claim 1, wherein the sensor coupled to the smart home controller includes a video camera in the dwelling, and wherein the first configuration has the video camera in the dwelling enabled, but notifications from the video camera in the dwelling disabled.

11. The method of claim 1, wherein the sensor coupled to the smart home controller includes a video camera in the dwelling, and wherein the second configuration has the video camera in the dwelling enabled, and notifications from the video camera in the dwelling enabled.

12. The method of claim 1, further comprising:

while operating in the first configuration and in accordance with a determination that
the door was locked from inside the dwelling, and
the dwelling is unoccupied,
setting or sending instructions to set the configuration of the smart home controller for the dwelling to the second configuration.

13. The method of claim 1, further comprising:

in accordance with a determination that
the door is unlocked, and
the dwelling is unoccupied,
setting or sending instructions to set the configuration of the smart home controller for the dwelling to the second configuration, including locking or sending instructions to lock one or more doors in the dwelling.

14. The method of claim 1, further comprising: sending a notification to a user that the smart home controller has been placed in the second configuration.

15. The method of claim 1, wherein a housing that contains a computer system also contains a door lock for the door.

16. The method of claim 1, wherein the sensor comprises a motion sensor and:

in the first configuration, the motion sensor is disabled and one or more window and/or door sensors communicatively coupled to the smart home controller are enabled; and in the second configuration, the motion sensor is enabled and the one or more window and/or door sensors are enabled.

17. A non-transitory computer readable storage medium storing one or more programs, the one or more programs comprising instructions, which when executed by a computer system, cause the computer system to:

receive, from a smart home controller, location data for the smart home controller being controlled by a user;

receive, from the smart home controller, door lock activation data;

set a configuration of a controller for a dwelling to a first configuration based at least in part on a determination that a door was locked from inside the dwelling based on the location data from the smart home controller being controlled by the user, wherein
the first configuration comprises disabling transmission to the controller of notifications generated based on data from a sensor while the sensor continues to monitor at least a portion of the dwelling; and set or send instructions to set the configuration of the smart home controller to a second configuration from the first configuration based at least in part on a determination that the door was locked from outside the dwelling based on the location data from the smart home controller being controlled by the user, wherein
the second configuration comprises enabling transmission to the smart home controller of notifications based on data generated by the sensor.

\* \* \* \* \*